(12) United States Patent
Hwang et al.

(10) Patent No.: US 8,809,564 B2
(45) Date of Patent: Aug. 19, 2014

(54) PLATINUM COMPLEX, MANUFACTURING METHOD THEREOF AND PLATINUM CATALYST CONSTRUCTED THEREBY

(75) Inventors: Weng-Sing Hwang, Tainan (TW); Shyh-Jiun Liu, Taipei County (TW); Chia-Hung Huang, Kaohsiung (TW); Chun-Kai Huang, Kaohsiung County (TW)

(73) Assignee: National Cheng Kung University, Tainan (TW)

( * ) Notice: Subject to any disclaimer, the term of this patent is extended or adjusted under 35 U.S.C. 154(b) by 1042 days.

(21) Appl. No.: 12/688,374

(22) Filed: Jan. 15, 2010

(65) Prior Publication Data

US 2011/0177937 A1    Jul. 21, 2011

(51) Int. Cl.
*C07F 15/00* (2006.01)
*B01J 31/18* (2006.01)

(52) U.S. Cl.
CPC ............ *B01J 31/1815* (2013.01); *B01J 31/183* (2013.01); *C07F 15/0053* (2013.01); *B01J 31/1805* (2013.01)
USPC ........................................................ 556/137

(58) Field of Classification Search
USPC ........................................................ 556/137
See application file for complete search history.

(56) References Cited

U.S. PATENT DOCUMENTS

| | | | |
|---|---|---|---|
| 4,136,059 A | 1/1979 | Jalan et al. | |
| 5,489,563 A | 2/1996 | Brand et al. | |
| 5,525,568 A | 6/1996 | Yamaguchi et al. | |
| 2007/0073197 A1 * | 3/2007 | Prausnitz et al. | 601/2 |

FOREIGN PATENT DOCUMENTS

| | | | | |
|---|---|---|---|---|
| TW | 565471 | * | 12/1991 | ............ B01T 23/38 |
| TW | 565471 | | 12/2002 | |

OTHER PUBLICATIONS

Sheng Zhang, Yuyan Shao, Geping Yin and Yuehe Lin, Stabilization of platinum nanoparticle electrocatalysts for oxygen reduction using poly(diallyldimethylammonium chloride) J. Mater. Chem., 2009, 19, 7995-8001.*

Cotton F.A. and Wilkinson G., "Advanced Inorganic Chemistry" 5th Ed., ch. 19., pp. 927-928, Wiley 1988.*
Kellar LR, Drugs Future, 1993, 18, 551.*
Kim N.-H., Hwang I.-C., and Ha K., Acta Cryst (2009) E65, m180, [doi:10.1107/S1600536809000725].*
Kim et al. doi:10.1107/S1600536809002694 Acta Cryst. (2009). E65, m230.*
Shyh-Jiun Liu et al., Chelating agent assisted microwave synthesis of carbon . . . fuel cells; Electrochemistry Communications, 2009, pp. 1792-1795, vol. 11(9).
Hans B. Jonassen et al., Inorganic Complex Compounds Containing Polydentate Groups. III. . . with Triethylenetetramine; J. Am. Chem. Soc., 1949, pp. 4097-4100, vol. 71(12).
Jorma Arpalahti et al., Kinetics of Complexation of Aquated PtII(dien) with Inosine and 1-Methylinosine as a function of pH; Inorganic Chemistry, 1990, pp. 2564-2567, vol. 29.
Roger Palmans et al.,Synthesis and Characterization of Bis(2,2'-bipyridyl)platinum(I):A Novel Microtubular Linear-Chain Complex;J.Am.Chem.Soc.,1998, pp. 12647-12653, vol. 118.
Fred Basolo et al., The Stereochemistry of Complex Inorganic Compounds. X. The . . . -(ethylenediamine)-platinum(IV) Chloride; J. AM. Chem. Soc., 1950, pp. 2433-2438, vol. 72 (6).
Liu et al, "Chelating agent assisted microwave synthesis of carbon supported Pt nanoparticles for low temperature polymer electrolyte fuel cells," Electrochemistry Communications, 2009, pp. 1792-1795, vol. 11.

* cited by examiner

*Primary Examiner* — Sudhakar Katakam
*Assistant Examiner* — Kofi Adzamli
(74) *Attorney, Agent, or Firm* — Muncy, Geissler, Olds & Lowe, P.C.

(57) ABSTRACT

A manufacturing method of a platinum complex is mixing chloroplatinic acid and a chelating agent with a solvent, wherein $[PtCl_6]^{2-}$ ions of the chloroplatinic acid is reacted with the chelating agent to form a platinum complex $Pt[R]^{2+}$, wherein the chelating agent(R) is selected from ethylenediamine, 1,10-phenanthroline, 2,2'-Bipyridine, diethylenetriamine, triethylenetetraamine, phenanthroline, or bipyridine. Moreover, a method for producing a platinum catalyst on supports is mixing the chloroplatinic acid, a chelating agent and supports with a solvent to form a platinum complex, which is incorporated onto the supports. Following, a reduction step and a drying step are processed to get the platinum catalyst on the supports.

1 Claim, 37 Drawing Sheets

PLATINUM COMPLEX, MANUFACTURING METHOD THEREOF AND PLATINUM CATALYST CONSTRUCTED THEREBY

BACKGROUND OF THE INVENTION

1. Field of the Invention

The present invention relates to a complex and an application thereof and, more particularly, to a platinum complex, a manufacturing method thereof, a platinum catalyst, and a platinum catalyst on supports constructed thereby.

2. Description of the Related Art

Platinum has a stable chemical property even in high temperature. Platinum will not react with oxygen, sulfide, strong acids or strong bases in room temperature. In current petrochemistry and energy industry, platinum (Pt) is used as catalysts.

In petrochemistry industry, Pt catalysts are used to increase amount of petroleum. Most of petroleum refineries have catalytic equipment coating with Pt catalysts. When vaporied crude oil flows through catalytic equipment, Pt will catalyze vaporied crude oil to any desired forms. Moreover, most of gas-cleaning facilities for vehicles use ceramic honeycomb coating with Pt and Pd alloy to transfer carbon monoxide (CO) and hydrocarbon into carbon dioxide and water.

In energy industry, shortage of global petroleum is getting serious. Therefore, the development of fuel cells for commercial purpose is attracting more attention. The fuel cells, especially proton exchange membrane fuel cells (PEMFC) are considered as a main source of green energy and only emits harmless carbon dioxide, water and air.

Hydrogen and oxygen are used as fuels of the fuel cells. Pt catalysts are coating on electrodes of the fuel cells so that the fuel cells can generate electrical energy by executing electrochemical reaction with catalytic action of Pt catalysts. In electrochemical reaction, hydrogen in anode side of the membrane electrode assembly (MEA) is decomposed into hydrogen ions and electrons. At the cathode side, oxygen is reacted with the hydrogen ions and the electrons to form water. If total surface area of catalysts can be increased, catalytic performance of Pt catalysts can be improved so that the reacting amount of hydrogen and oxygen per unit area can be increased. Therefore, current density can be increased.

However, in nature, Pt generally exists in a form of a pure state. As a result, surface area of Pt in the form of the pure state can not reach requirement for catalysts. Therefore, further processes are needed to obtain nanoparticles of Pt catalysts. By increasing surface area of Pt, using amount of Pt catalysts can be reduced.

Conventional manufacturing method of Pt catalysts is using chloroplatinic acid as a raw material to produce nanoparticles of Pt catalysts. Usually, chloroplatinic acid can be obtained by dissolving Pt in aqua regia with over amount of hydrochloric acid (HCl) wherein aqua regia is a mixing solution of nitric acid and hydrochloric acid with volume ratio 1:3. Due to chlorine ions in aqua regia can induce the formation of a Pt complex, $[PtCl_6]^{2-}$, Pt can be dissolved in aqua regia. Reaction equation is shown as following: $3\ Pt+16\ H^++4\ NO^{3-}+18\ Cl^- \square\ 3\ [PtCl_6]^{2-}+4NO+8\ H_2O$. Next, the Pt complex, $[PtCl_6]^{2-}$ is reacted with sodium nitrate ($NaNO_3$) to generate PtO in the temperature 500° C. Following the reduction reaction, PtO is heated to 560° C. for pyrolysis so that PtO can be reduced to form Pt catalysts.

Conventional manufacturing method of Pt catalysts as described above, the oxidation-reduction reaction is taken place between $[PtCl_6]^{2-}$ and $NaNO_3$ to produce PtO. However, Pt (II) ions of PtO are very active so that random aggregation between Pt (II) ions happens easily. Therefore, the number of aggregation between Pt (II) ions is hard to control. After completing the reduction reaction, particle sizes of Pt catalysts are still too big and the distribution of particle sizes is too wide so that surface area of Pt and uniformity can not be increased. Moreover, the stability and catalytic activity are low.

In order to solve problems described above, another conventional manufacturing method of Pt catalysts is provided. Pt is absorbed onto supports with the high electrical conductivity such as carbon black to form Pt catalysts on the supports. By dispersing Pt on the supports, stability, catalytic activity, surface area and ability to bear loading can be enhanced.

Currently, using carbon black as the supports has been studied for several years. Catalysts of carbon-black-supported Pt can be abbreviated as Pt/C catalysts, and Pt/C catalysts have well dispersion, fine particles and low manufacturing method etc. Pt/C catalysts are commonly used in proton exchange membrane fuel cell (PEMFC).

Conventional manufacturing method of Pt/C catalysts is dissolving chloroplatinic acid in a deionized water acting as a solvent and then mixing a suitable amount of carbon black into the solvent to get a solution. After the solution is stirred well, the solvent is evaporated. Following, in the reduction reaction, hydrogen is used as reductant to form Pt/C catalysts.

However, in the above conventional manufacturing method of Pt/C catalysts, the reduction reaction is executed right after chloroplatinic acid is mixed with carbon black so that random aggregation between Pt (II) ions still happens easily. Therefore, particle size distribution is still too wide and Pt (II) ions are easy to agglomerate. Furthermore, dispersion of Pt/C catalysts is not even so that surface area of Pt/C catalysts still can not be increased resulting in low catalytic activity.

Taiwan Patent No. 565471 entitled "Processing of high-performance platinum catalyst" illustrates another conventional manufacturing method of Pt/C catalysts. Chloroplatinic acid is dissolved in deionized water and then adding sodium carbonate, and sodium bisulfate into deionized water orderly to form a mixing solution. Following, more sodium carbonate is added into the mixing solution to form a precipitate of $Na_6Pt(SO_3)_4$. Next, the precipitate of $Na_6Pt(SO_3)_4$ is dissolved in water and put into an ion exchange resin to replace sodium ions with hydrogen ions and obtain a solution of the precipitate having Pt (II) ion. Following, carbon black, which is graphited in high temperature, is added into the solution of the precipitate and stirred well. Following, hydrogen peroxide ($H_2O_2$) acting as a reactant is added in a reduction reaction step. Besides, a drying step is executed by filtering the solution of the precipitate to get the precipitate and then a dried precipitate is obtained by baking. Finally, hydrogen is used in the reduction reaction with temperature being limited between 200 and 250° C. so that Pt/C catalysts with uniform dispersion and small particle size can be obtained.

However, the above conventional manufacturing method of Pt/C catalysts is still directly mixing chloroplatinic acid with carbon black and then processing the reduction reaction to get Pt/C catalysts. Therefore, random aggregation between Pt (II) ions still happens easily resulting in the wide distribution of particle sizes and poor dispersion etc. Therefore, overall surface area of Pt/C catalysts is still too small and catalytic activity thereof is low. Moreover, this conventional method is focused on interaction between carbon black and Pt, which used to consider as keypoint to affect dispersion, growth and structure of Pt particles. In fact, controlling Pt particles within a narrow distribution should be the most important factor to affect catalytic activity of Pt/C catalysts, current density and power of the fuel cells.

SUMMARY OF THE INVENTION

The primary objective of the present invention is to provide a platinum complex, which is formed by engaging Pt ions with a chelating agent to increase the stability of the platinum complex.

Another objective of the present invention is to provide a manufacturing method of the platinum complex, by controlling the combination reaction between Pt ions to let Pt ions disperse evenly.

A further objective of the present invention is to provide a manufacturing method of a platinum catalyst obtained through the platinum complex, so that a range in particle size of the platinum catalyst is narrow and the uniformity of particles of the platinum catalyst can be increased.

Still another objective of the present invention is to provide a manufacturing method of the platinum catalyst obtained through the platinum complex, so that the dispersion of particles of the platinum catalyst can be enhanced.

Yet another objective of the present invention is to provide a manufacturing method of the platinum catalyst obtained through the platinum complex, so that surface area of the platinum catalyst can be increased to improve the catalytic activity.

To accomplish the above objective, the present invention provides a platinum complex with a form of $Pt[R]^{2+}$, wherein R is selected from ethylenediamine, 1,10-phenanthroline, 2,2'-Bipyridine, diethylenetriamine, triethylenetetraamine, phenanthroline, or bipyridine.

According to the present invention, a manufacturing method of a platinum complex is provided, which comprises: mixing chloroplatinic acid and a chelating agent with a solvent, wherein $[PtCl_6]^{2-}$ ions of chloroplatinic acid is reacted with the chelating agent to form a platinum complex.

According to the present invention, a manufacturing method of a platinum catalyst obtained through a platinum complex is provided, which comprises: a chelating step mixing a chloroplatinic acid and a chelating agent with a solvent to form a platinum complex solution, wherein $[PtCl_6]^2$ ions of chloroplatinic acid is reacted with the chelating agent to form a platinum complex; a reduction step adding a reductant into the platinum complex solution to form a suspension so that the platinum complex can be reduced to form Pt nanoparticles; and a drying step drying Pt nanoparticles after the reduction to obtain a platinum catalyst.

According to the present invention, a manufacturing method of a platinum catalyst obtained through the platinum complex is provided, which comprises: a chelating step mixing chloroplatinic acid, a chelating agent, and supports with a solvent to form a platinum complex solution with the supports, wherein $[PtCl_6]^{2-}$ ions of chloroplatinic acid is reacted with the chelating agent to form a platinum complex which is incorporated onto the supports; a drying step removing the solvent from the iron complex solution with the supports to form a dried iron complex on the supports; and a reduction step adding a reductant into the platinum complex solution with the supports to form a suspension so that the platinum complex which is incorporated onto the supports can be reduced to form Pt nanoparticles on the supports; and a drying step drying Pt nanoparticles on the supports after the reduction to obtain a platinum catalyst on the supports.

Further scope of the applicability of the present invention will become apparent from the detailed description given hereinafter. However, it should be understood that the detailed description and specific examples, while indicating preferable embodiments of the invention, are given by illustrations only, since various will become apparent to those skilled in the art from this detailed description.

BRIEF DESCRIPTION OF THE DRAWINGS

The present invention can be fully understood from the detailed description given herein below and the accompanying drawings which are given illustrations only, and thus are not limitative of the present invention, and wherein.

Figure 1:
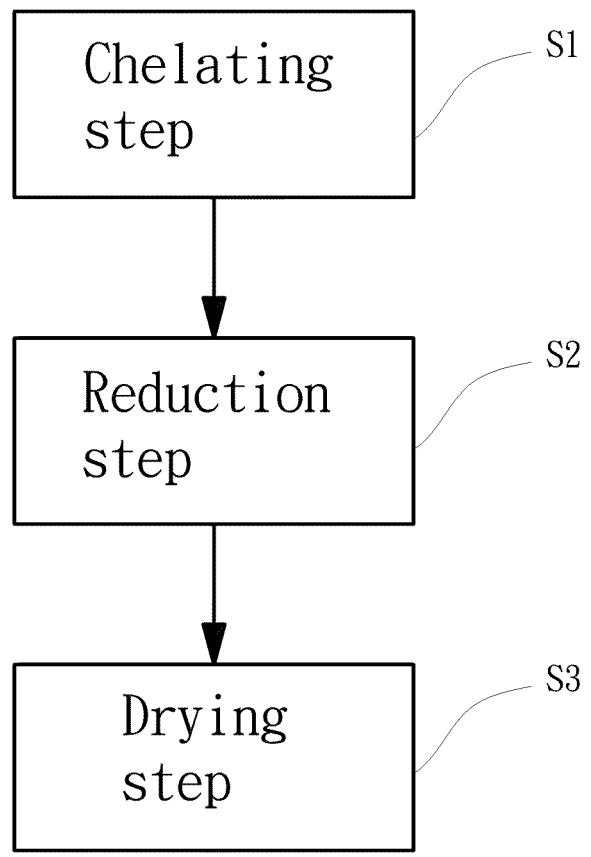
FIG. 1 is a flow chart of a manufacturing method of a platinum catalyst in accordance with a preferred embodiment of the present invention.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions that conform to specify the forces of weight, strength, and similar requirements will likewise be within the skill of the art after the following teachings of the present invention have been read and understood.

Where used in the various figures of the drawings, the same numerals that designate the same or similar parts. Furthermore, when the to rms "first", "second", "third", "fourth", "fifth", "sixth", "seventh", "eighth", "ninth", and similar terms are used herein, it should be understood that these terms have reference only to the structure shown in the drawings as it would appear to a person viewing the drawings and are utilized only to facilitate describing the invention.

DETAILED DESCRIPTION OF THE INVENTION

The present invention is focused on forming a platinum complex and using the platinum complex as precursor for making a platinum catalyst and a platinum catalyst on supports.

A. A Manufacturing Method of the Platinum Complex of the Present Invention

The manufacturing method of the platinum complex of a preferred embodiment according to the preferred teachings of the present invention includes a chelating step S1. The chelating step S1 is mixing chloroplatinic acid ($H_2PtCl_6 \cdot 6H_2O$) and a chelating agent with a solvent to form a platinum complex solution. Chloroplatinic acid is dissolved in the solvent to get $[PtCl_6]^{2-}$ ions for reacting with the chelating agent, so that $[PtCl_6]^{2-}$ ions can be engaged in the chelating agent to form the platinum complex. The solvent can be selected from water, ethanol, ether or acetonein etc., and is water or ethanol-water solution preferably. The chelating agent is selected from ethylenediamine ($NH_2CH_2CH_2NH_2$), 1,10-phenanthroline ($C_{12}H_8N_2$), 2,2'-Bipyridine ($C_{10}H_8N_2$), diethylenetriamine ($NH_2CH_2CH_2NHCH_2CH_2NH_2$), triethylenetetraamine ($NH_2CH_2CH_2NHCH_2CH_2NHCH_2CH_2NH_2$), phenanthroline ($C_{12}H_8N_2$), or bipyridine ($C_{10}H_8N_2$) etc. For simplifying description, the chelating agent with abbreviated form is shown as below. Ethylenediamine is denoted as "en", 1,10-phenanthroline is denoted as "phen", and 2,2'-bipyridine is denoted as "bpy" with the coordination number of 2; Diethylenetriamine is denoted as "dien" with the coordination number of 3; Triethylenetetraamine is denoted as "trien" with the coordination number of 4.

In detail, the chelating step S1 of the manufacturing method of the platinum complex as described above, the mole ratios of the chelating agent to Pt is preferably limited between 1:1 and 3:1 so that $[PtCl_6]^{2-}$ ions can be engaged in the chelating agent to form the platinum complex. For example, when the chelating agent is diethylenetriamine, the mole ratios of the chelating agent to Pt prefer to be limited between 1:1 and 2:1 to get the platinum complex in a preferred form of $Pt[dien]_2^{2+}$. When the chelating agent is triethylenetetraamine, the mole ratios of the chelating agent to Pt is preferably limited between 1:1 and 1.5:1 to get the platinum complex in a preferred form of $Pt[trien]^{2+}$. When the chelating agent is ethylenediamine, the platinum complex in a preferred form of $Pt[en]^{2+}$ can be obtained. When the chelating agent is 2,2'-Bipyridine, the platinum complex in a preferred form of $Pt[bpy]_2^{2+}$ can be obtained. When the chelating agent is 1,10-phenanthroline, the platinum complex in a preferred form of $Pt[phen]_2^{2+}$ can be obtained. Furthermore, when the chelating agent is selected from ethylenediamine, 2,2'-Bipyridine, or 1,10-phenanthroline, the mole ratios of the chelating agent to Pt is preferably limited between 2:1 and 3:1. So far, the manufacturing method of the platinum complex can be completed to get the platinum complex of the present invention.

Furthermore, the manufacturing method of the platinum complex according to the preferred teachings of the present invention further includes continuously stirring during mixing chloroplatinic acid and the chelating agent with the solvent. More particularly, the solvent is under stirring condition until all of chloroplatinic acid and the chelating agent are added into the solvent to get a well-mixed solution. After thoroughly stirred, the solution is preferably sonicated for 4 to 6 hours to let the solution be more uniformly blended, and the best time period of sonication is 4 hours.

According to the description above, by selecting various chelating agents, different forms of the platinum complex can be obtained. The platinum complex can further be used as a precursor. Platinum ions are easy to reduce to Pt. Furthermore, combining reaction between platinum ions takes place easily so that the bonding number between platinum ions varies. According to the preferred teachings of the present invention, platinum ions are engaged in the chelating agent so that combination between platinum ions is difficult; therefore, the platinum complex can be formed with being highly dispersed in the solution.

Moreover, in the previously disclosed manufacturing method of the platinum complex of the preferred embodiment according to the preferred teachings of the present invention has platinum ions as a central cation of the platinum complex. The surrounding ligands are the chelating agents. The chelating agent with nitrogen donor atoms gives stable low-spin, octahedral, or distorted octahedral complexes.

Complex is a structure consisting of a central atom or ion, bonded to a surrounding array of molecules or anions. The molecules or anions surrounding the central atom are called ligands. Ligands are generally bound to the central atom by a coordinate covalent bond (donating electrons from a lone electron pair into an empty metal orbital), and are thus said to be coordinated to the atom. Ligands can be divided into monodentate ligands such as $NH_3$, $F^-$, $Cl^-$, $CO$, $CN^-$ or $H_2O$ etc. and polydentate ligands. Complexes of polydentate ligands are called chelate complexes. They tend to be more stable than complexes derived from monodentate ligands. This enhanced stability, the chelate effect, is usually attributed to effects of entropy, which favors the displacement of many ligands by one poly dentate ligand. Therefore, selection of the chelating agent can be changed according to the coordination number of the chelating agent. Types of the chelating agent of the present invention are not limited to chelating agents described above.

B. The Platinum Complex of the Present Invention

According to the manufacturing method of the platinum complex as described above, one general form of the platinum complex is $Pt[R]^{2+}$, wherein R is selected from diethylenetriamine, triethylenetetraamine, ethylenediamine, 2,2'-Bipyridine, 1,10-phenanthroline, bipyridine, or phenanthroline to obtain the platinum complex in the forms of $Pt[dien]^{2+}$, $Pt[trien]^{2+}$, $Pt[en]^{2+}$, $[Pt(bpy)_2]^{2+}$, and $[Pt(phen)_2]^{2+}$ respectively. The platinum complex of the present invention can be evenly dispersed in the solution. Therefore, the platinum complex can be further applied on automobile converters etc.

The manufacturing method of the platinum complex according to the teachings of the present invention can get the uniform platinum complex. The platinum complex can be further used on manufacturing the platinum catalyst to improve uniformity and dispersion of the platinum catalyst.

C. A Manufacturing Method of a Platinum Catalyst Obtained Through One of the Above Platinum Complexes:

A manufacturing method of the platinum catalyst obtained through the platinum complex of a preferred embodiment according to the preferred teachings of the present invention is shown in FIG. 1. The manufacturing method of the platinum catalyst obtained through the platinum complex comprises a chelating step S1, a reduction step S2, and a drying step S3 to form the platinum catalyst.

The chelating step S1 is mixing chloroplatinic acid ($H_2PtCl_6 \cdot 6H_2O$) and a chelating agent with a solvent to form a platinum complex solution. Chloroplatinic acid is dissolved in the solvent to get $[PtCl_6]^{2-}$ ions for reacting with the chelating agent, so that $[PtCl_6]^{2-}$ ions can be engaged in the chelating agent to form the platinum complex. The chelating step S1 of the manufacturing method of the platinum catalyst obtained through the platinum complex is the same as the manufacturing method of the platinum complex and, thus, not described in detail to avoid redundancy. In the chelating step S1, the chelating agent is used to confine platinum ions so that bonding between platinum ions is getting more difficult. Therefore, the growth of platinum can be controlled to form the platinum complex suspensed in the solvent uniformly. As a result, the well-distributed platinum complex solution can be obtained.

The reduction step S2 is to add a reductant into the platinum complex solution to form a suspension so that the platinum complex can be reduced to form Pt nanoparticles. In detail, the reductant is formaldehyde (HCHO), preferably. The mole ratio of formaldehyde to chloroplatinic acid is preferable to be 20:1. Formaldehyde is used as the reductant to let the platinum complex in the platinum complex solution be reduced to Pt wherein Pt is suspended in the platinum complex solution to form the suspension. Moreover, the mole ratio of the chelating agent to Pt will affect the ability of the reduction and particle size distribution. If the amount of the chelating agent is used too much, reduction of platinum complex to Pt nanoparticles will be difficult. If the available amount of the chelating agent is not enough, particle size distribution for Pt nanoparticles will not be uniform. Therefore, the mole ratios of the chelating agent to Pt prefer to be limited between 1:1 and 3:1.

Furthermore, reduction of platinum ions in alkaline solution is better than in acid solution. In alkaline solution, the uniformity of Pt nanoparticles after the reduction can be improved. Therefore, during the reduction step S2, after the reductant is added into the platinum complex solution to form the suspension, an alkaline solution is gradually added into the suspension until PH of the suspension is more than 7. The alkaline solution is preferably selected from 0.5M of sodium hydroxide (NaOH). PH of the present invention is preferably limited between 12 and 14, and the best PH is located at 14.

After adjusting PH until PH of the suspension is more than 7 as described above, the suspension is preferably further executed sonication to get well-mixed solution. The time period of sonication is preferably between 0.2 to 5 hours, and the best time period is 30 minutes.

In addition, after the reductant is added into the platinum complex solution, the suspension is preferably exposed in the middle of a microwave oven for 3 to 30 minutes at 700 W for a microwave process, and the best time period is 6 minutes. By the microwave process, the suspension can be heated up quickly so that the efficiency of transformation in the reduction can be enhanced and the dispersion of Pt nanoparticles can be improved.

Furthermore, after the suspension is heated up by the microwave process, the suspension is preferably allowed to cool to the room temperature so that particle size of the Pt nanoparticles after the reduction can be more uniform and Pt nanoparticles can be precipitated in the suspension.

The drying step S3 is to dry Pt nanoparticles after the reduction to obtain the platinum catalyst. In detail, after separating the precipitate from the suspension, the precipitate is dried in a vacuum oven to get the platinum catalyst. The temperature for executing the drying step S3 is preferably limited between 373K and 423K. If the temperature is lower than 373K, the solvent retaining in the precipitate is hard to remove. If the temperature is higher than 423K, the pyrolysis of the precipitate of platinum happens easily so that Pt might disappear. The time period of the drying step S3 is preferably between 1 to 24 hours. According to the preferred teachings of the present invention, the platinum catalyst is preferably formed a perfect sphere. So far, the manufacturing method of the platinum catalyst can be completed to get the platinum catalyst of the present invention.

Figure 2:
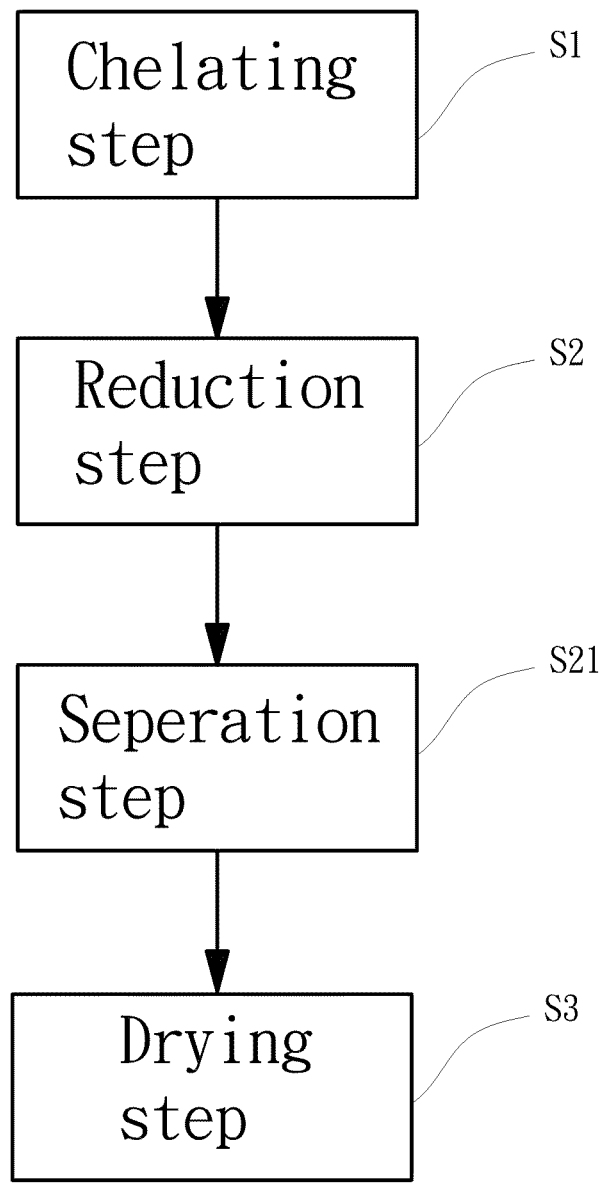
FIG. 2 is a flow chart of a manufacturing method of the platinum catalyst further including a separation step in accordance with the preferred embodiment of the present invention.

Furthermore, referring to FIG. 2, after completing the reduction step S2, a separation step S21 can be further executed, preferably. The separation step S21 is to separate the precipitate of platinum from the suspension before the drying step S3 is executed. In detail, the precipitate of platinum was isolated from the suspension by centrifugation and then the precipitate is washed with ethanol ($C_2H_5OH$) and deionized water so that the precipitate can be completely separated from the suspension.

According to the manufacturing method of the platinum catalyst obtained through the platinum complex as described above, in the chelating step S1, platinum ions are confined by the chelating agent to lower bonding ability between central platinum ions of the platinum complex to let the platinum complex be well distributed in the solvent. Therefore, the bonding number of central platinum ions can be controlled to improve dispersion, uniformity, and the growth of Pt nanoparticles.

Furthermore, the platinum complex of the present invention can be further used as the precursor for production of the platinum catalyst. In detail, the platinum is incorporated onto the supports to form the platinum catalyst on supports to increase surface area of the platinum catalyst and ability of loading. Therefore, the platinum complex can be further applied on the manufacturing method of the platinum catalyst on supports.

Figure 3:
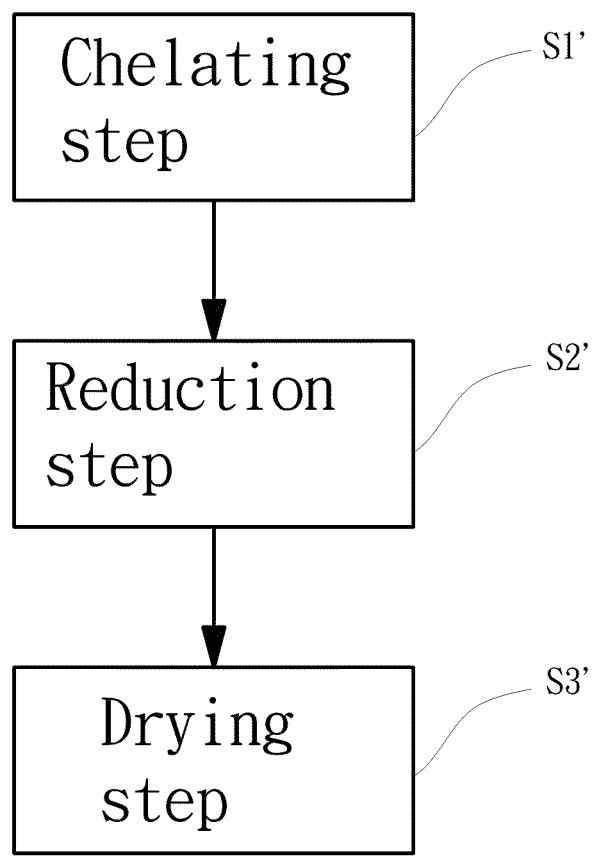
FIG. 3 is a flow chart of a manufacturing method of a platinum catalyst on supports in accordance with a preferred embodiment of the present invention.

D. A Manufacturing Method of a Platinum Catalyst on Supports Obtained Through the Platinum Complex of the Present Invention:

A manufacturing method of the platinum catalyst on the supports obtained through the platinum complex of a preferred embodiment according to the preferred teachings of the present invention is shown in FIG. 3. The manufacturing method of the platinum catalyst on the supports through the platinum complex comprises a chelating step S1', a reduction step S2', and a drying step S3' to form the platinum catalyst on the supports.

The chelating step S1' is mixing chloroplatinic acid, a chelating agent, and supports with a solvent to form a platinum complex solution with the supports. Chloroplatinic acid is dissolved in the solvent to get $[PtCl_6]^{2-}$ ions for reacting with the chelating agent, so that $[PtCl_6]^{2-}$ ions can be engaged in the chelating agent to form the platinum complex. Then, the platinum complex is incorporated onto the supports. The chelating step S1' of the manufacturing method of the platinum catalyst on the supports obtained through the platinum complex is the same as the manufacturing method of the platinum complex and, thus, not described in detail to avoid redundancy.

Furthermore, the supports are preferably selected from various porous materials, which are further divided into two types, microporous materials and macroporous materials. Microporous materials include powder of silica, carbon black, zinc oxide, and silicon carbide etc. Macroporous materials include diatomite, floatstone, alumina, active carbon, and silica etc. The supports used in the present invention are better to be carbon black or silica etc. According to the preferred teachings of the present invention, carbon black is used as the supports of the platinum catalyst to increase surface area and dispersion of the platinum catalyst. Furthermore, by using carbon black as the supports, amount of the platinum catalyst used in the fuel cell can be reduced to lower manufacturing cost. Sequence for adding chloroplatinic acid, the chelating agent, and carbon black can be changed. Chloroplatinic acid and the chelating agent are added to the solvent, and carbon black can be loaded therebefore or thereafter. Furthermore, chloroplatinic acid, the chelating agent, and the supports also can be added into the solvent in the same time. Therefore, $[PtCl_6]^{2-}$ ions of chloroplatinic acid can be reacted with the chelating agent to form the platinum complex which is incorporated onto surface of the supports so that dispersion of the platinum complex can be enhanced. Following, the reduction step S2' can be processed.

Moreover, it is better to preclean the supports by hydrochloric acid (HCl) to remove metal impurity therein before the supports are added into the solvent. Then, because chloride will affect formation of particle size of the platinum nanoparticles, deionized water is used to remove chloride in the supports so that the platinum catalyst can be well distributed on the supports. Moreover, in order to increase dispersion and avoid agglomeration of the supports in the solvent, the supports are added to ethanol and mix well first before adding into the solvent. Therefore, platinum after reduction can be dispersed uniformly on the supports to get the platinum catalyst on the supports with narrow distribution of nanoparticles.

As described above, in the chelating step S1', chloroplatinic acid, the chelating agent, and the supports are added into the solvent under continuously stirring in the solvent to get the platinum complex solution with the supports. Then, it is preferably to sonicate the platinum complex solution with the supports for 4 to 6 hours; especially, for 4 hours to enhance uniformity of the platinum complex solution with the supports.

Referring to FIG. 3 again, regarding the reduction step S2' of the manufacturing method of the platinum catalyst on the supports obtained through the platinum complex according to the preferred teachings of the present invention, a reductant is added into the platinum complex solution to form a suspension so that the platinum complex can be reduced to form Pt nanoparticles on the supports. Following processes of the reduction step S2' are substantially the same as those of the reduction step S2 and, thus, not described in detail to avoid redundancy.

The drying step S3' is to dry a precipitate of Pt nanoparticles after the reduction to obtain the platinum catalyst on the supports. In detail, after separating the precipitate from the suspension, the precipitate is dried in a vacuum oven to get the platinum catalyst on the supports. Following processes of the drying step S3' are substantially the same as those of the drying step S3 and, thus, not described in detail to avoid redundancy. So far, the manufacturing method of the platinum catalyst on the supports obtained through the platinum complex of the present invention can be completed. According to the preferred teachings of the present invention, nanoparticles of the platinum catalyst on the supports is uniformly dispersed with narrow distribution of particle size.

Figure 4:
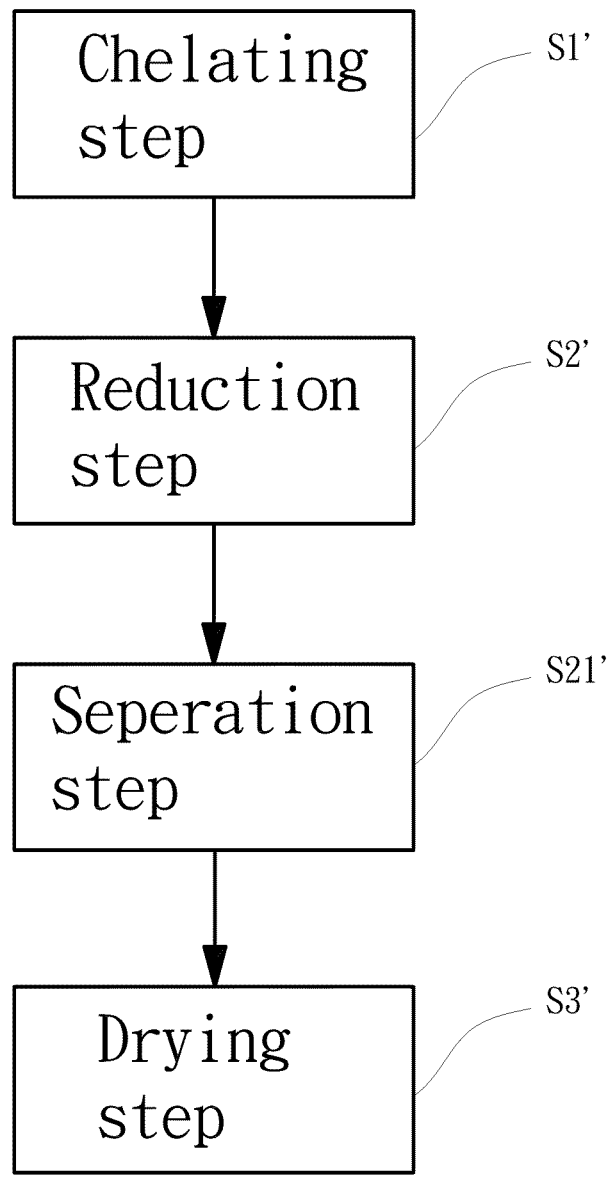
FIG. 4 is a flow chart of a manufacturing method of the platinum catalyst on the supports further including a separation step in accordance with the preferred embodiment of the present invention.

In addition, referring to FIG. 4, after completing the reduction step S2', a separation step S21' can be further executed, preferably. The separation step S21' is to separate the precipitate of platinum with the supports from the suspension before the drying step S3' is executed. Following is substantially the same as described above and therefore not described in detail to avoid redundancy.

E. Detail Embodiments of the Manufacturing Method of the Platinum Catalyst on the Supports According to the Preferred Teachings of the Present Invention:

The manufacturing method of the platinum catalyst on the supports of a first example according to the preferred teachings of the present invention is illustrated as the following. Preferably, carbon black is used as the supports to form the platinum catalyst on the supports. For following easy description, the platinum catalyst with carbon black as the supports is abbreviated as Pt/C-x, wherein "x" represents types of the chelating agent. The coordination number of the chelating agent to Pt can be 2 to 4 etc. According to types of the chelating agents, which have various coordination numbers, several kinds of the platinum complexes can be formed.

Figure 5:
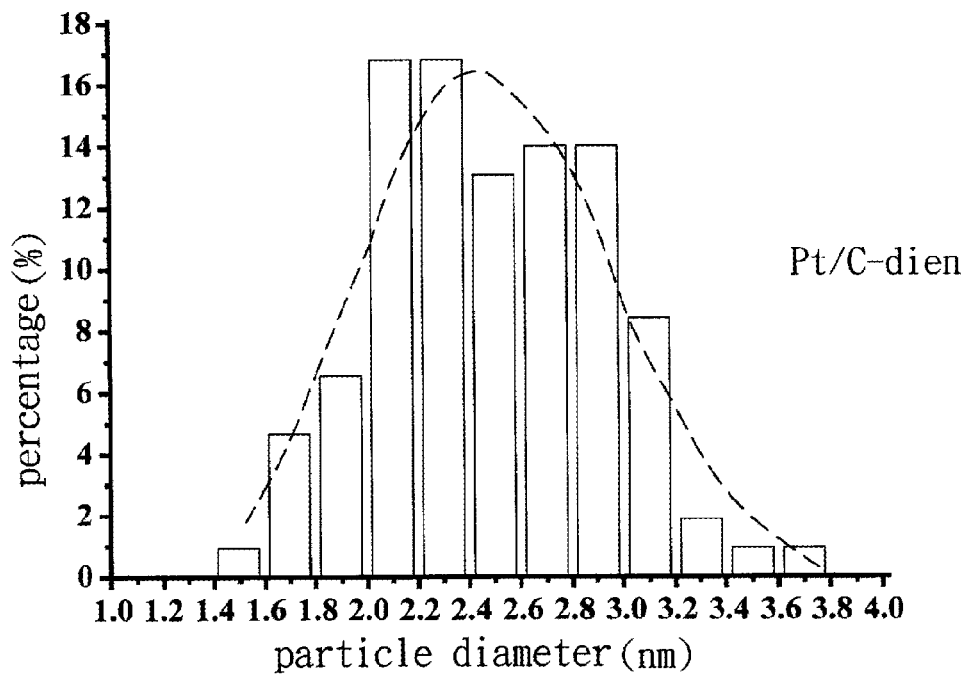
FIG. 5 is histograms of the particle size distribution for a Pt/C-dien catalyst in accordance with the preferred embodiment of the present invention.
Figure 10A:
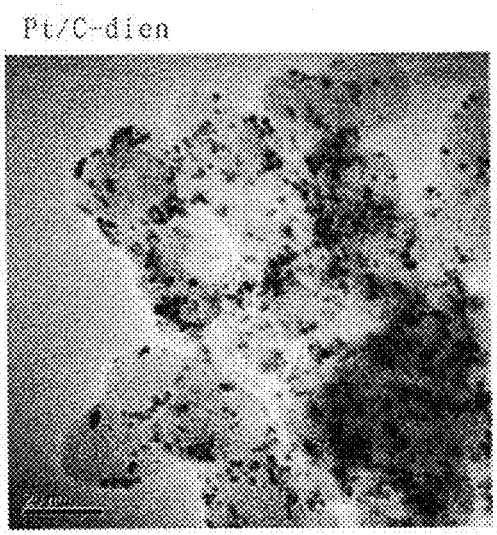
FIGS. 10a-10c are TEM images of the Pt/C-dien catalyst by using diethylenetriamine as a chelating agent at various magnifications in accordance with a first example of the present invention.
Figure 10B:
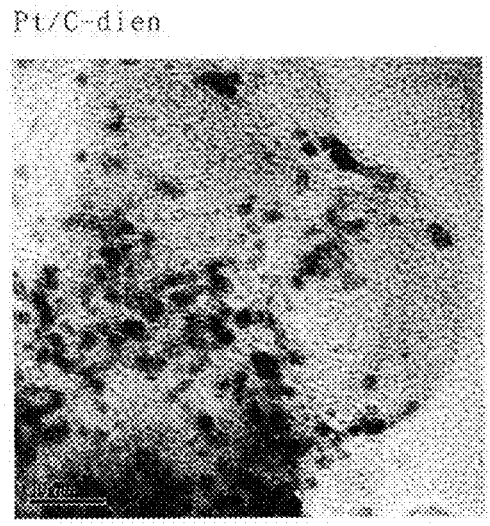
Figure 10C:
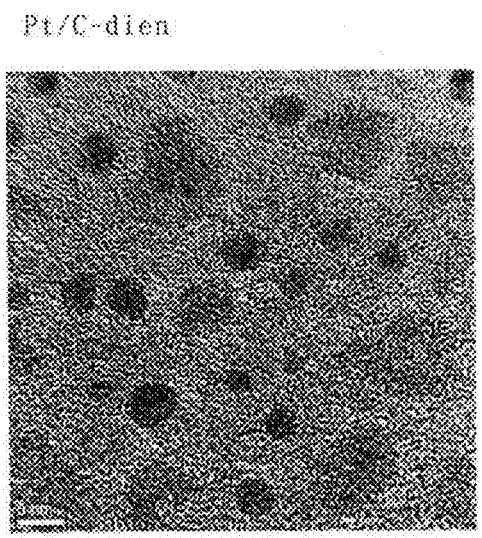
Figure 10D:
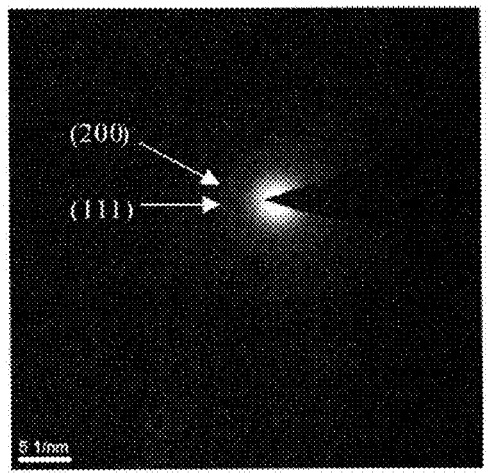
FIG. 10d is selected area electron diffraction patterns (SADP) of the Pt/C-dien catalyst by using diethylenetriamine as the chelating agent in accordance with the first example of the present invention.

The manufacturing method of the platinum catalyst on the supports of the first example according to the preferred teachings of the present invention, during the chelating step S1', diethylenetriamine is used as a chelating agent and water is used as a solvent. Carbon black, Vulcan XC-72, with 450 mg is used as the supports. The solvent is under continuously stirring condition until all of chloroplatinic acid ($H_2PtCl_6$) and the chelating agent are added into the solvent and mixed well to form a platinum complex of $Pt[dien]^{2+}$, wherein the chelating agent with 18 mg and chloroplatinic acid with 26.1 ml are used. Moreover, the supports are cleaned by 6M of HCl and deionized water to remove impurities from carbon black and then the supports are mixed with 10 ml of ethanol before adding into the solvent to form a platinum complex solution with the supports. 0.2 mmol of the platinum complex of $Pt[dien]^{2+}$ is incorporated onto carbon black. For thoroughly mixed, the platinum complex solution with the supports is sonicated for 4 hours to get a paste. The loading of Pt with respect to carbon black is about 15%. Following, the reduction step S2' is processed. After thorough stirring and sonication for 4 hours, 5.2 ml of 37% formaldehyde (HCHO) with a mole ratio of $HCHO:H_2PtCl_6=20:1$ is added into the paste to form a suspension. Then, 25 ml of 0.5 M NaOH solution is then gradually added to the suspension until the pH of the suspension reached 14. Following, after 30 min of sonication, the suspension is exposed in the middle of a microwave oven for 6 min at 700 W and then naturally cooled to room temperature so that the platinum complex which is incorporated onto the supports can be reduced to platinum with the supports, which precipitates in the suspension. Then, the separation step S21' is processed to separate platinum with the supports from the suspension by centrifugation. Platinum with the supports is washed with $C_2H_5OH$ and deionized water, and then dried in a vacuum oven at 423K overnight to obtained the platinum catalyst on the supports, which is abbreviated as a Pt/C catalyst. The crystalline structure of the platinum catalyst on the supports is fcc structure. Referring to FIG. 5, particle size distribution of the first example of Pt/C-dien catalyst is between 1.5 and 3.7 nm. A mean particle size of Pt/C-dien catalyst is 2.5 nm. Standard deviation is 0.5 nm. As a result, particle size distribution of the present invention is narrow. Besides, referring to FIGS. 10a to 10c, according to various magnifications of TEM, Pt nanoparticles is highly dispersed on the supports of carbon black. Particle size distribution is based on the measurements of 300 particles selected from random regions. The average particle sizes of the platinum catalysts are estimated using the Scherrer equation.

Figure 6:
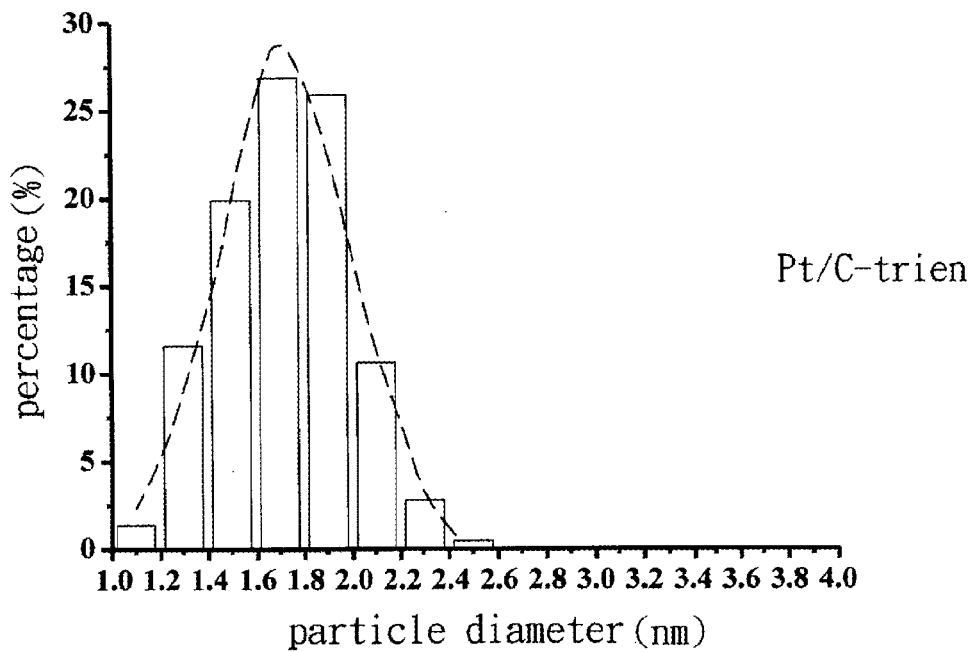
FIG. 6 is histograms of the particle size distribution for a Pt/C-trien catalyst in accordance with the preferred embodiment of the present invention.
Figure 11A:
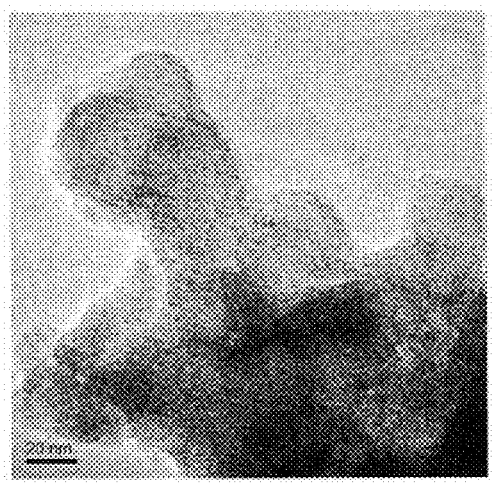
FIGS. 11a-11c are TEM images of the Pt/C-trien catalyst by using triethylenetetraamine as the chelating agent at various magnifications in accordance with a second example of the present invention.
Figure 11B:
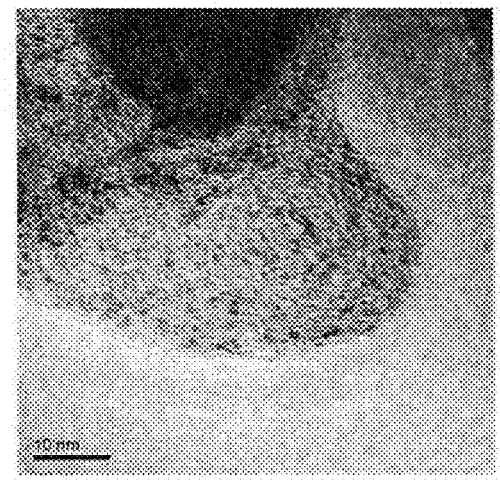
Figure 11C:
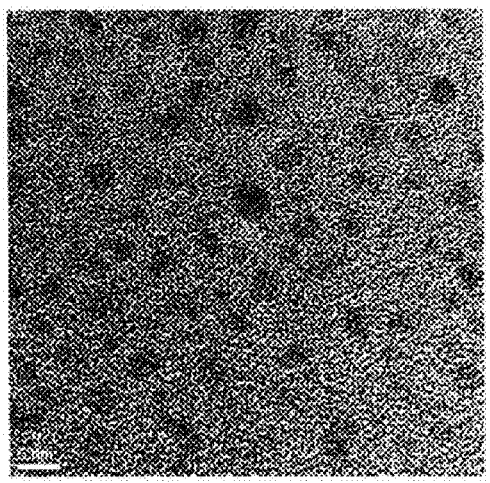
Figure 11D:
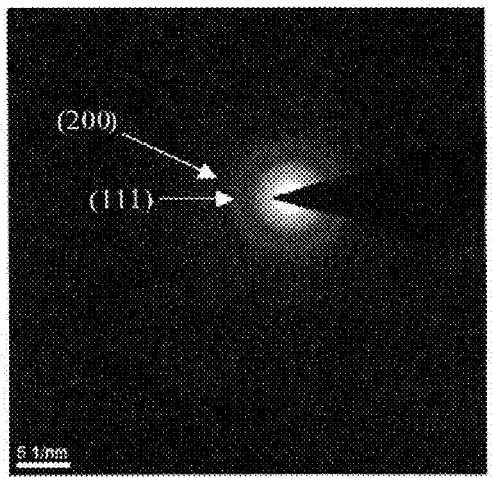
FIG. 11d is selected area electron diffraction patterns (SADP) of the Pt/C-trien catalyst by using triethylenetetraamine as the chelating agent in accordance with the second example of the present invention.

The manufacturing method of the platinum catalyst on the supports of a second example according to the preferred teachings of the present invention is the same as the first example as described above and therefore not described in detail to avoid redundancy. The only difference between the second and the first examples is that the chelating agent used in the second example is triethylenetetraamine to form the platinum complex of $Pt[trien]^{2+}$ wherein the chelating agent with 25 mg and chloroplatinic acid with 26.1 ml are used. Referring to FIG. 6, particle size distribution of the second example of Pt/C-trien catalyst is between 1.1 and 2.5 nm. The mean particle size of Pt/C-trien catalyst is 1.7 nm. The standard deviation is 0.3 nm. As a result, particle size distribution of the present invention is narrow. Besides, referring to FIG. 11a to 11c, according to various magnifications of TEM, Pt nanoparticles is highly dispersed on the supports of carbon black.

Figure 7A:
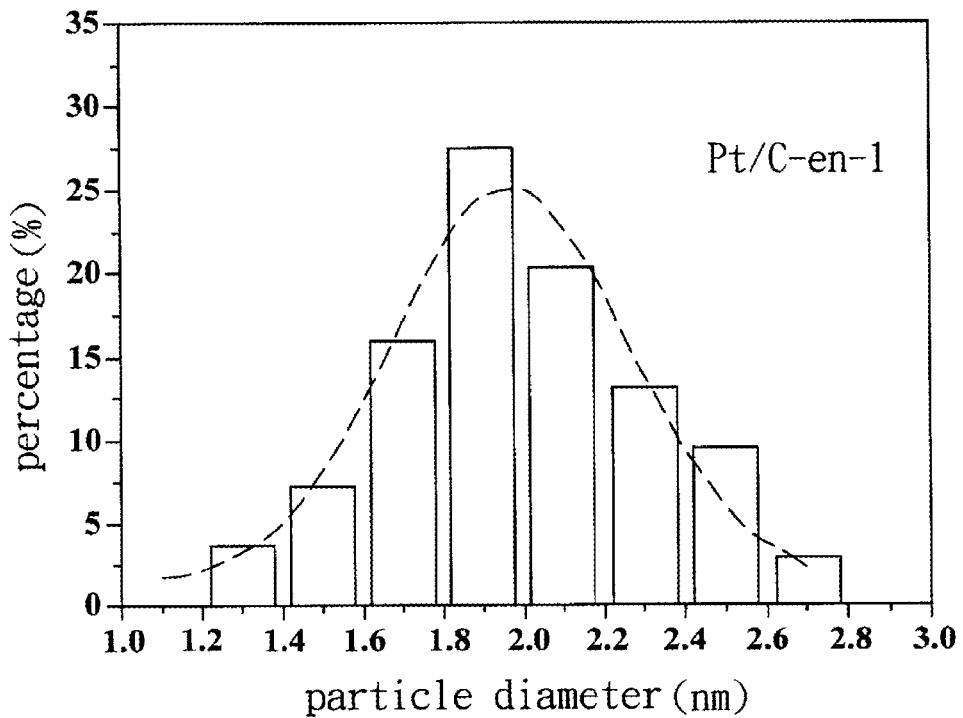
FIGS. 7a-c are histrograms of the particle size distribution for a Pt/C-en catalyst in accordance with the preferred embodiment of the present invention.
Figure 12A:
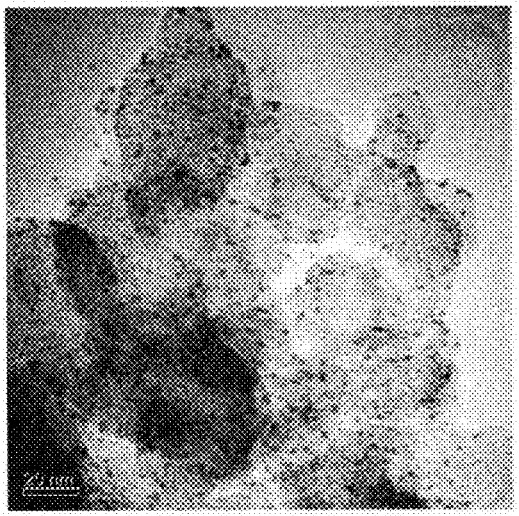
FIGS. 12a-12c are TEM images of the Pt/C-en catalyst by using ethylenediamine as the chelating agent at various magnifications in accordance with a third example of the present invention.
Figure 12B:
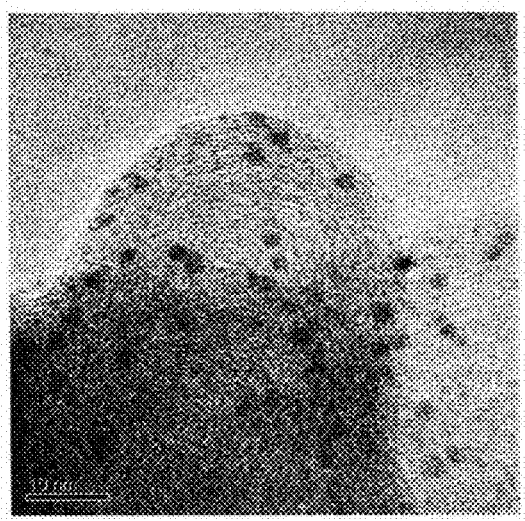
Figure 12C:
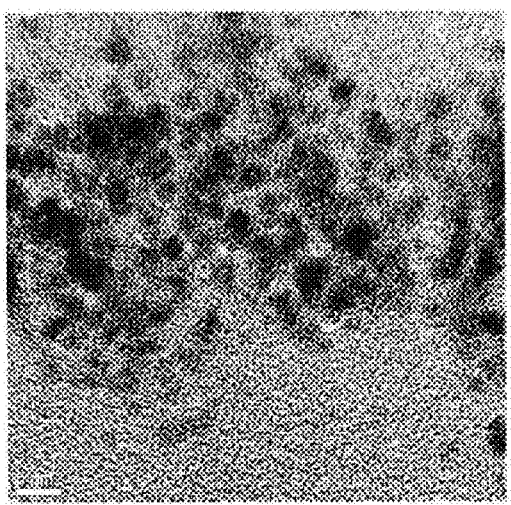
Figure 12D:
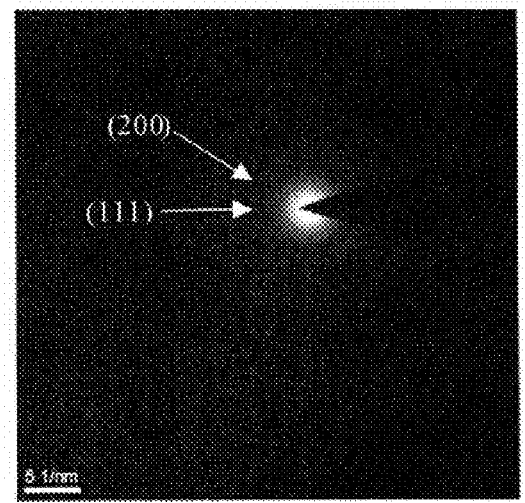
FIG. 12d is selected area electron diffraction patterns (SADP) of the Pt/C-en catalyst by using ethylenediamine as the chelating agent in accordance with the third example of the present invention.

The manufacturing method of the platinum catalyst on the supports of a third example according to the preferred teachings of the present invention is the same as the first example as described above and therefore not described in detail to avoid redundancy. The only difference between the third and the first examples is that the chelating agent used in the third example is ethylenediamine to form the platinum complex of $Pt[en]_2^{2+}$ wherein the chelating agent with 20 mg and chloroplatinic acid with 26.1 ml are used. Referring to FIG. 7a, particle size distribution of the third example is between 1.3 and 2.7 nm. The mean particle size is 2.0 nm. The standard deviation is 0.3 nm. As a result, particle size distribution of the present invention is narrow. Besides, referring to FIGS. 12a to 12c, according to various magnifications of TEM, Pt nanoparticles are highly dispersed on the supports of carbon black.

TABLE 1 nanoparticle size, particle size distribution, and Pt loading according to various Pt/C catalyst

| Precursor | Pt/C-x | Particle size (nm) | Standard deviation (nm) | Particle size distribution (nm) | Pt loading (wt. %) |
|---|---|---|---|---|---|
| $Pt[dien]^{2+}$ | Pt/C-dien | 2.5 | 0.5 | 1.5~3.7 | 12.6 |
| $Pt[trien]^{2+}$ | Pt/C-trien | 1.7 | 0.3 | 1.1~2.5 | 9.8 |
| $Pt[en]_2^{2+}$ | Pt/C-en | 2 | 0.3 | 1.1~2.5 | 8 |
| — | Pt/C-ETEK | 2.6 | — | 1.2~4.3 | 20 |

Figure 7B:
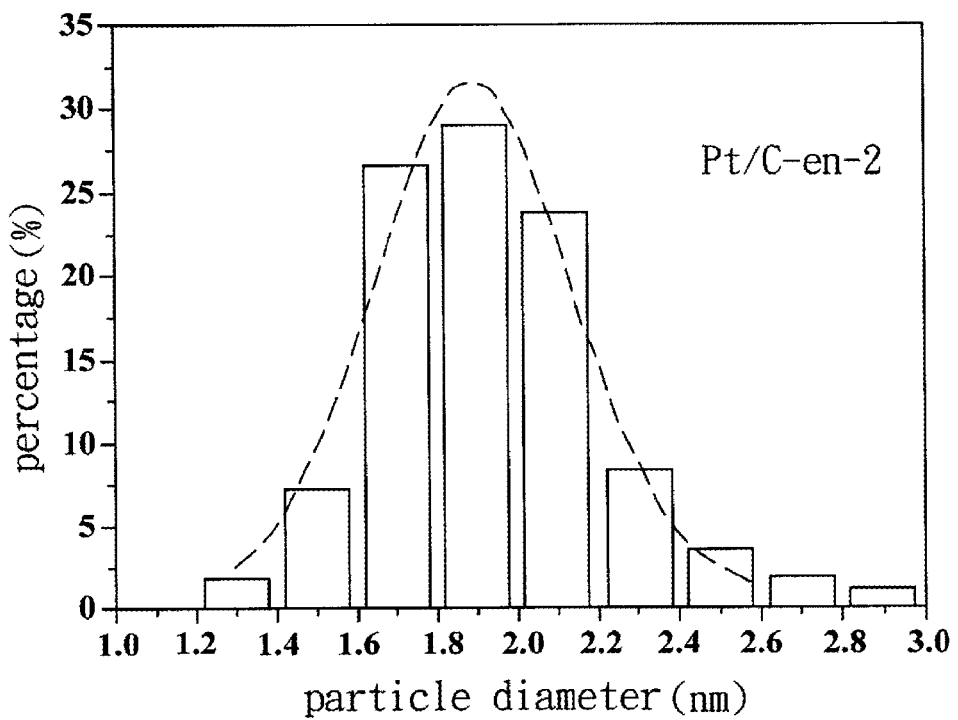
Figure 7C:
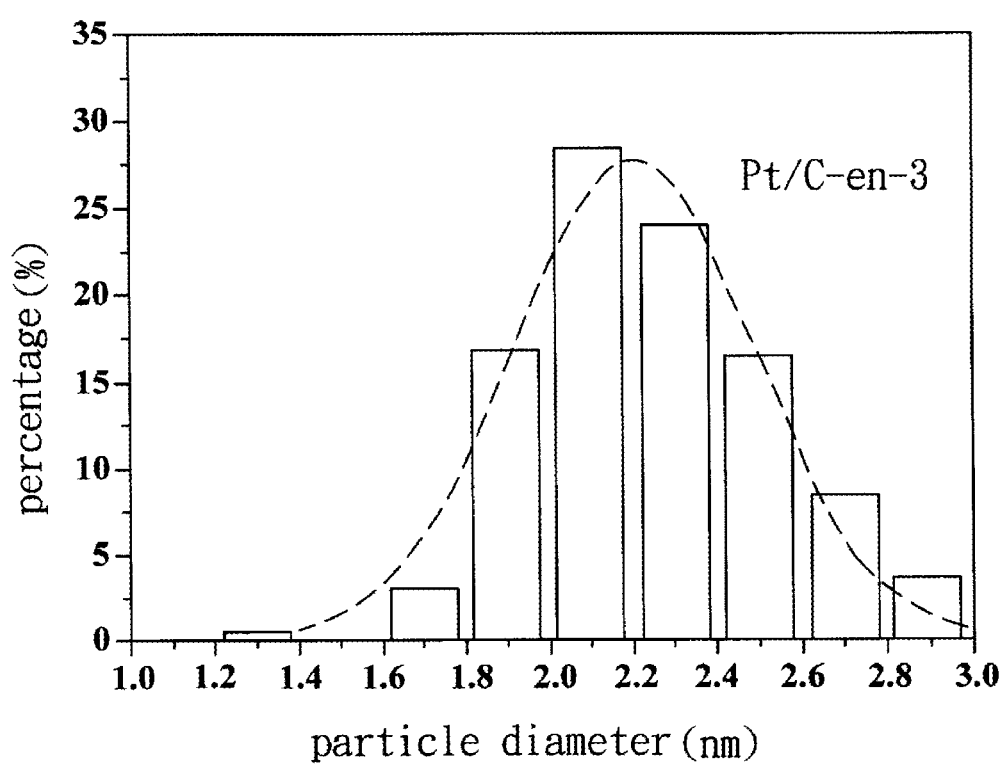

Regarding to table 1 and FIGS. 5 to 7, The order of mean particle size is Pt/C-ETEK (a commercial Pt-based catalyst) >Pt/C-dien>Pt/C-en>Pt/C-trien. The platinum complex of $Pt[trien]^{2+}$ is about $10^3$ times more thermodynamic stable than the platinum complex of $Pt[dien]^{2+}$. The platinum complex of $Pt[trien]^{2+}$ has three connected five-member chelating rings and four nitrogen atoms, which are coordinated to one Pt central ion. The platinum complex of $Pt[dien]^{2+}$ has two connected five-member and three nitrogen atoms, which are coordinated to one Pt central ion. Thermodynamic stable affects the speed of the reduction so that particle size and particle size distribution will also be affected. The speed of the reduction of $Pt[trien]^{2+}$ is slower than $Pt[dien]^{2+}$ so that particle size and particle size distribution thereof is smaller than $Pt[dien]^{2+}$. Besides, Pt loading in a chloroplatinic acid solution can be measured by inductively-coupled plasma spectrometer (ICP-AES) wherein the chloroplatinic acid solution is prepared by 1 g of solid chloroplatinic acid and 100 ml deionized water. From the result of ICP-AES, Pt loading in the chloroplatinic acid solution is 431.7 mg.

The manufacturing method of the platinum catalyst on the supports of a fourth example according to the preferred teachings of the present invention is the same as the first example as described above and therefore not described in detail to avoid redundancy. The only difference between the fourth and the first examples is that the chelating agent used in the fourth example is ethylenediamine to form the platinum complex of $Pt[en]_2^{2+}$ wherein the loading of Pt with respect to carbon black is 0.33, 0.67, 1 mmol for Pt/C-en-1, Pt/C-en-2, and Pt/C-en-3 catalysts, respectively. Moreover, the mole ratio of the chelating agent to Pt is 2:1. Besides, the solvent of the fourth example is an ethanol-water solution which the ratio of ethanol to water is 1:4. According to the table 2 below, all of nanoparticle size and particle size distribution of the platinum catalyst of the present invention with various Pt loading are better than Pt/C-ETEK. For example, nanoparticle size and particle size distribution of the Pt/C-en-3 with 30.2 wt. % Pt loading are still smaller than Pt/C-ETEK. As a result, even increasing Pt loading of the platinum catalyst, well-distributed platinum catalyst without agglomeration still can be obtained. Besides, regarding to table 2 and FIGS. 7a to 7c, particle size distribution of the platinum catalyst is narrow and the dispersion thereof is uniform.

TABLE 2 nanoparticle size, particle size distribution, and yield according to various Pt loading by the chelating agent of ethylenediamine.

| Pt/C-x | Particle size (nm) | Particle size distribution (nm) | Pt loading (wt. %) | Yield (%) |
| --- | --- | --- | --- | --- |
| Pt/C-en-1 | 1.9 | 1.2~3.0 | 7.6 | 52 |
| Pt/C-en-2 | 2.0 | 1.3~2.7 | 17.8 | 79 |
| Pt/C-en-3 | 2.2 | 1.6~3.0 | 30.2 | 99 |
| Pt/C-ETEK | 2.6 | 1.2~4.3 | 20 | — |

Figure 8:
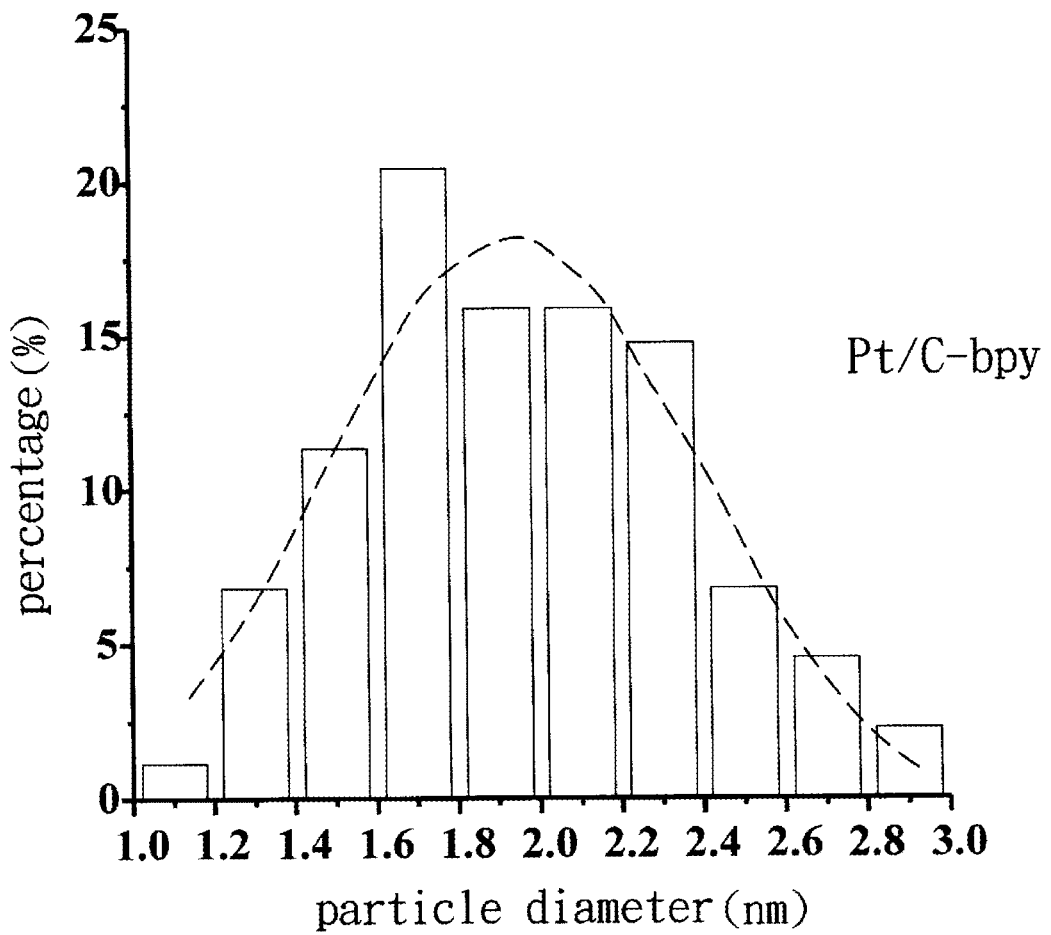
FIG. 8 is histrograms of the particle size distribution for a Pt/C-bpy catalyst in accordance with the preferred embodiment of the present invention.
Figure 13A:
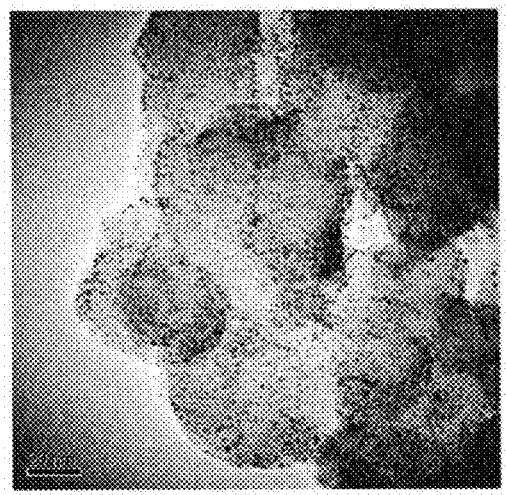
FIGS. 13a-13c are TEM images of the Pt/C-bpy catalyst by using ethylenediamine as the chelating agent at various magnifications in accordance with a fifth example of the present invention.
Figure 13B:
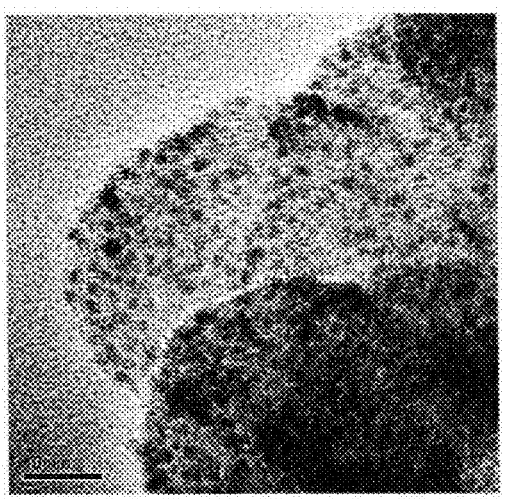
Figure 13C:
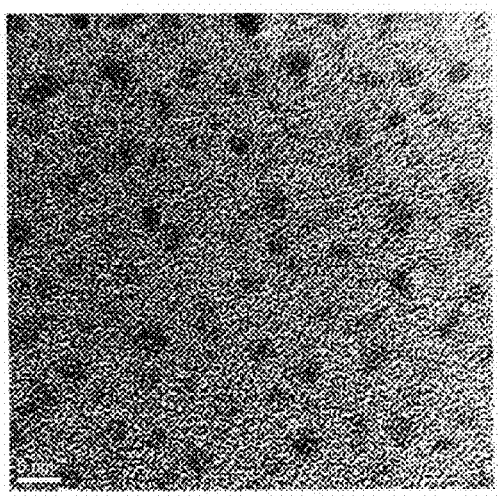
Figure 13D:
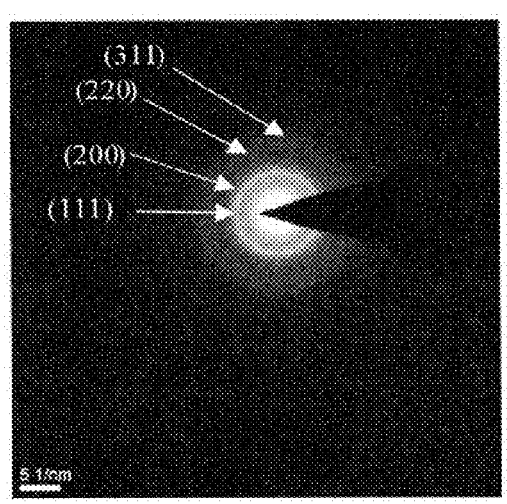
FIG. 13d is selected area electron diffraction patterns (SADP) of the Pt/C-bpy catalyst by using 2,2'-Bipyridine as the chelating agent in accordance with the fifth example of the present invention.
Figure 14A:
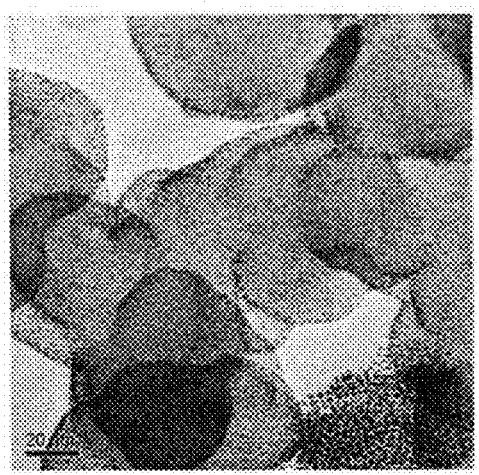
FIGS. 14a-14k are TEM images of a Pt/C-phencatalyst by using 1,10-phenanthroline as the chelating agent with 21.4% Pt loading in various areas in accordance with a seventh example of the present invention.
Figure 14B:
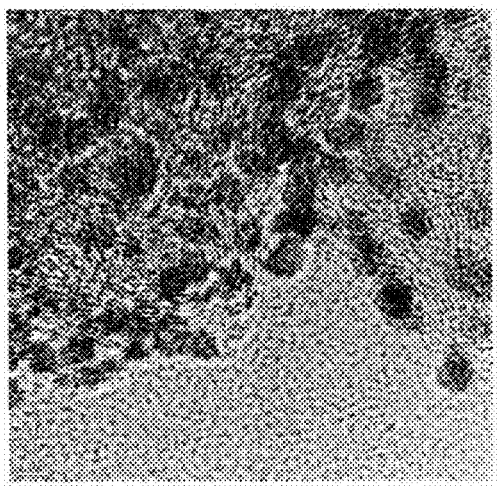
Figure 14C:
Figure 14D:
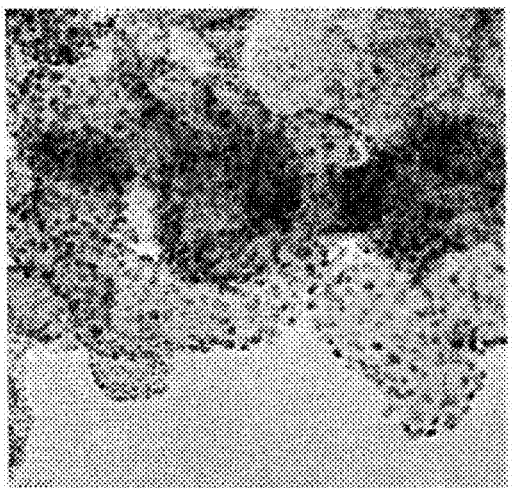
Figure 14E:
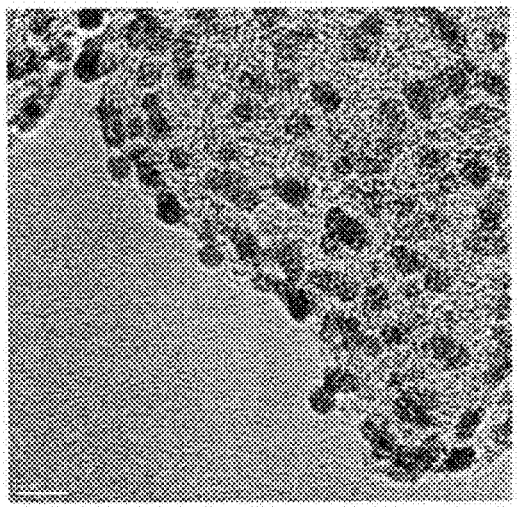
Figure 14F:
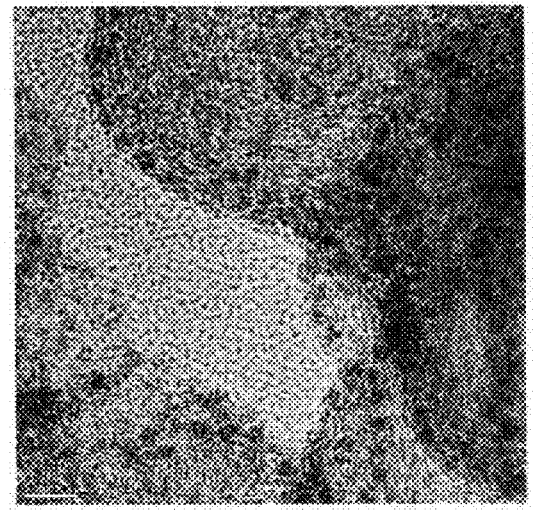
Figure 14G:
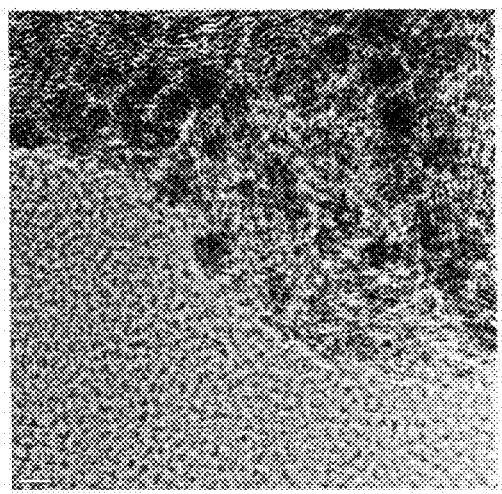
Figure 14H:
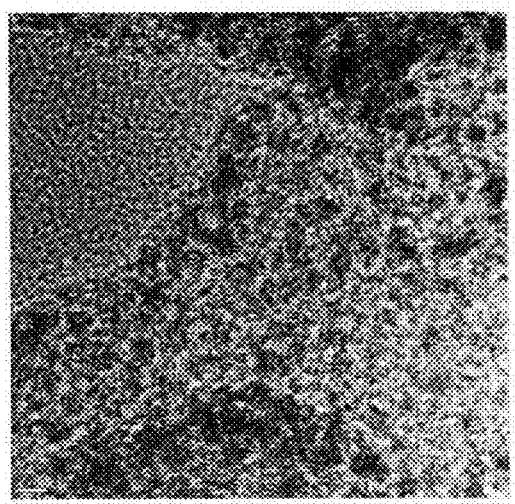
Figure 14I:
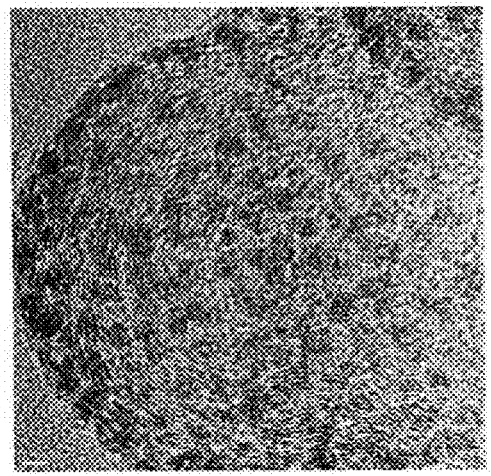
Figure 14J:
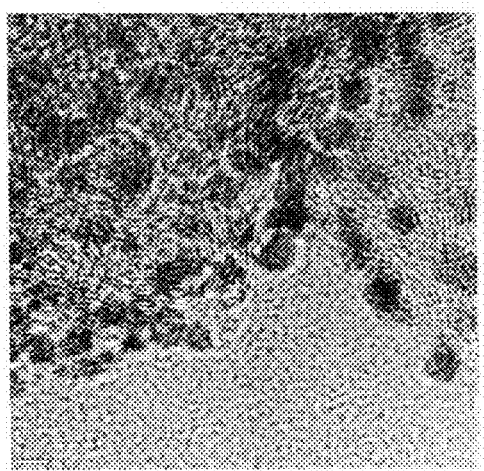
Figure 14K:
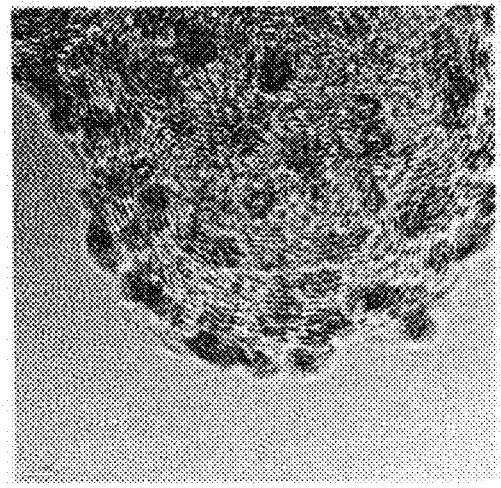
Figure 15A:
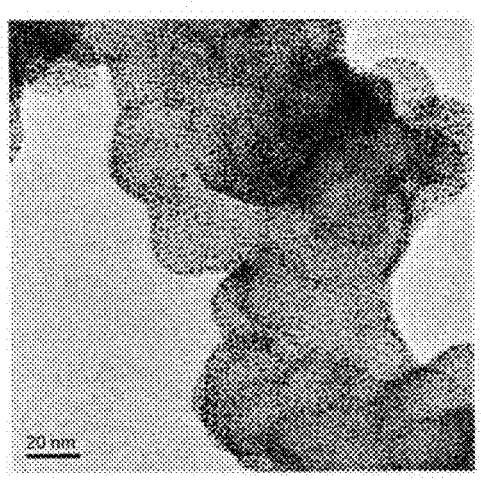
FIGS. 15a-15k are TEM images of a Pt/C-phencatalyst by using 1,10-phenanthroline as the chelating agent with 30% Pt loading in various areas in accordance with the seventh example of the present invention.
Figure 15B:
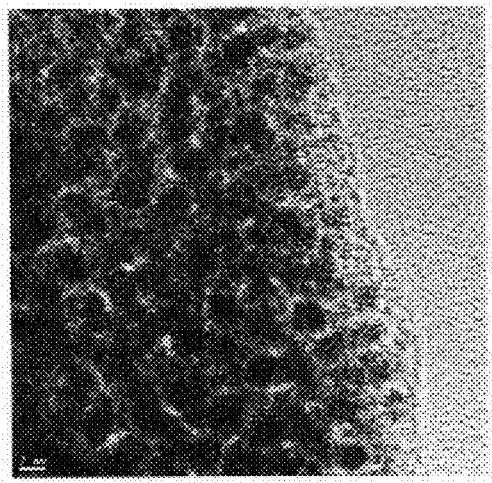
Figure 15C:
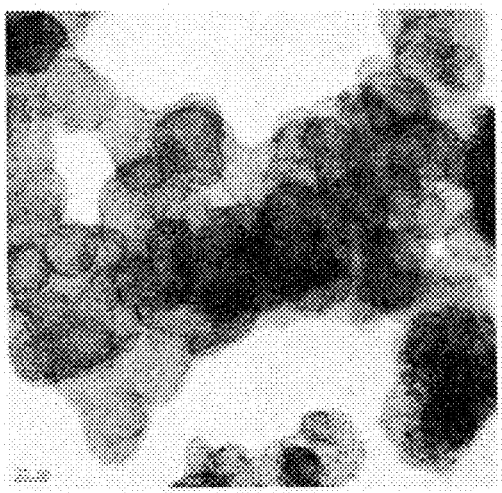
Figure 15D:
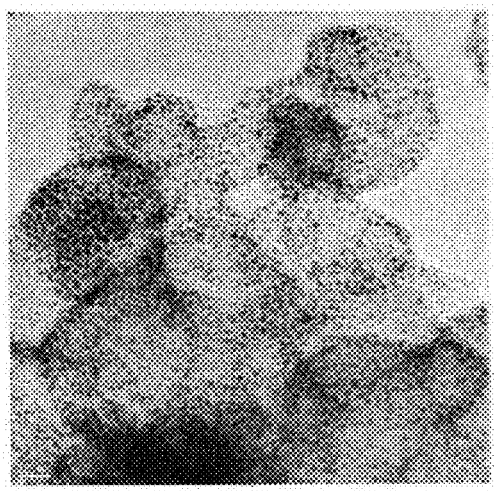
Figure 15E:
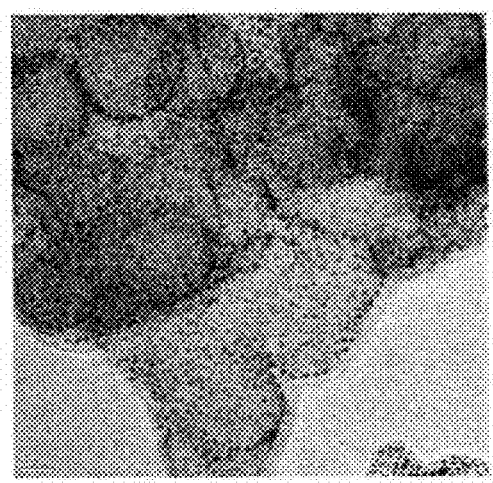
Figure 15F:
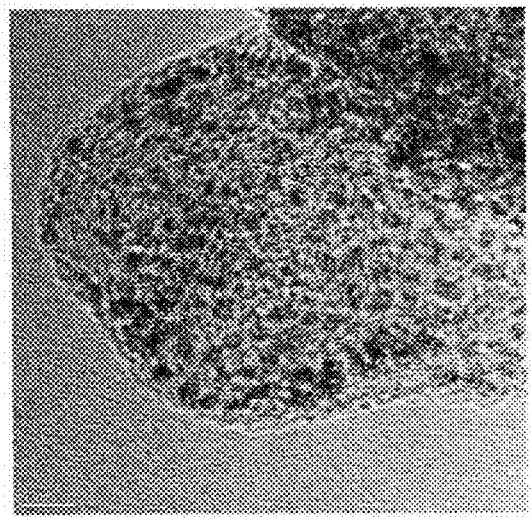
Figure 15G:
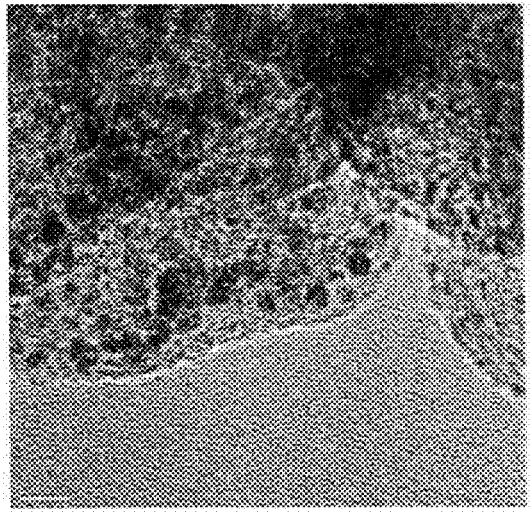
Figure 15H:
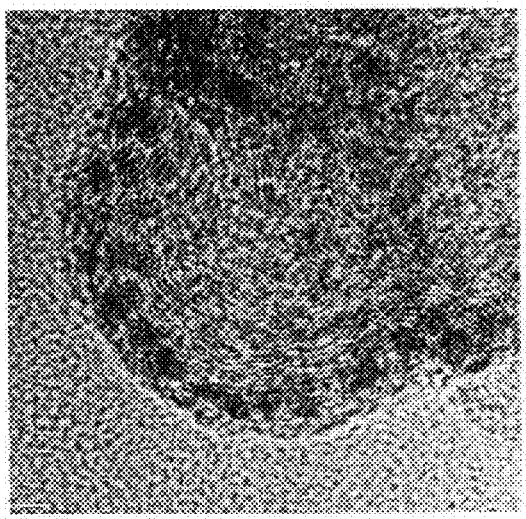
Figure 15I:
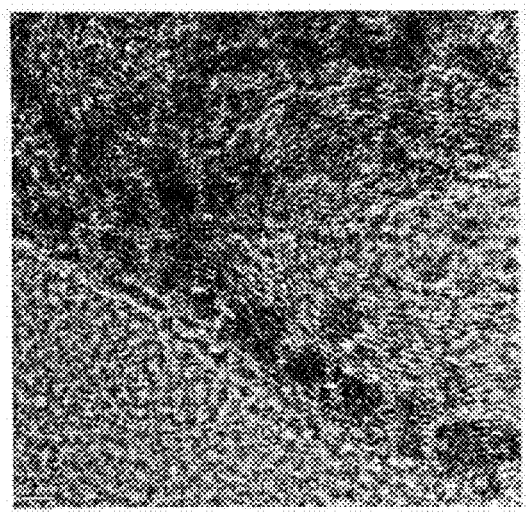
Figure 15J:
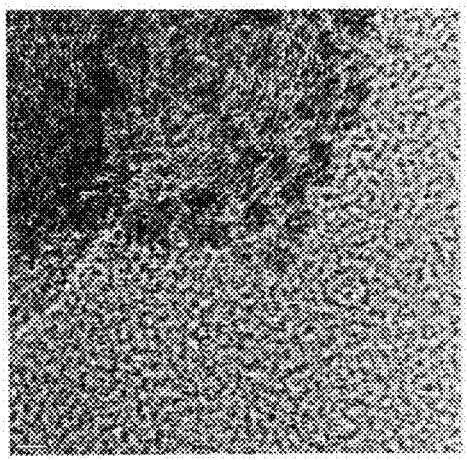
Figure 15K:
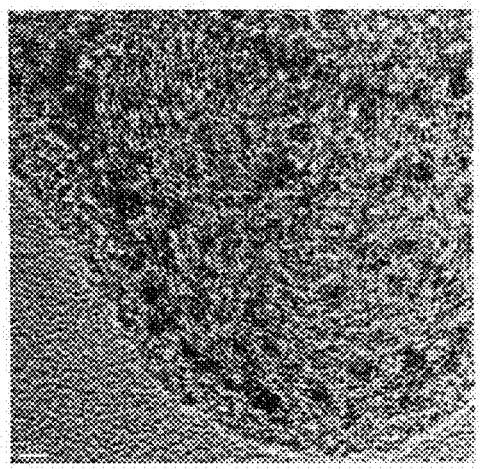
Figure 16A:
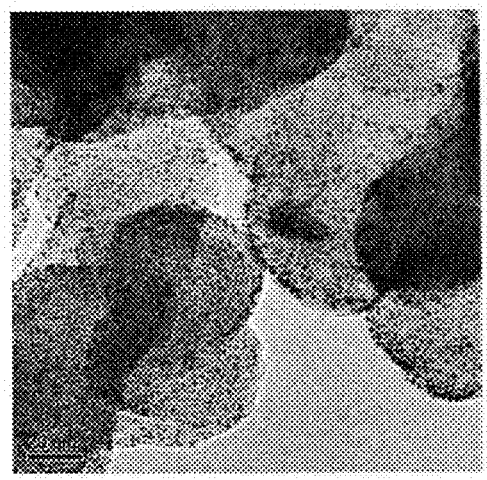
FIGS. 16a-16i are TEM images of a Pt/C-trien catalyst by using triethylenetetraamine as the chelating agent with 15.5% Pt loading in various areas in accordance with a eighth example of the present invention.
Figure 16B:
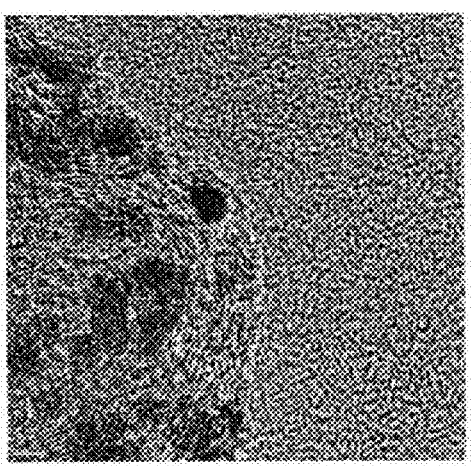
Figure 16C:
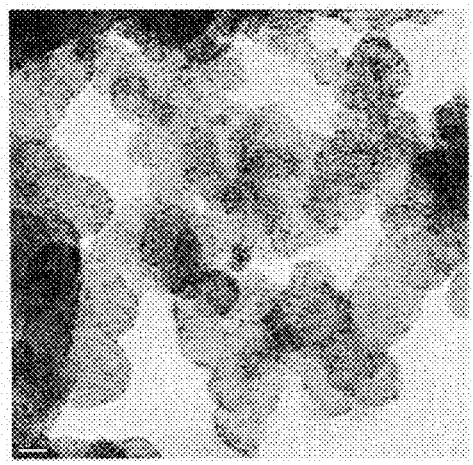
Figure 16D:
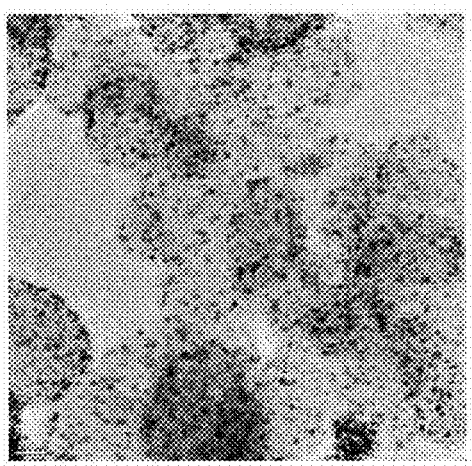
Figure 16E:
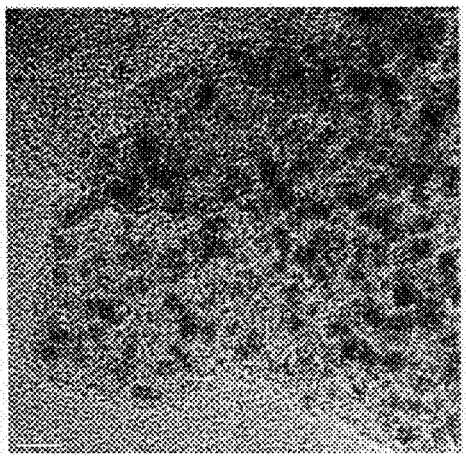
Figure 16F:
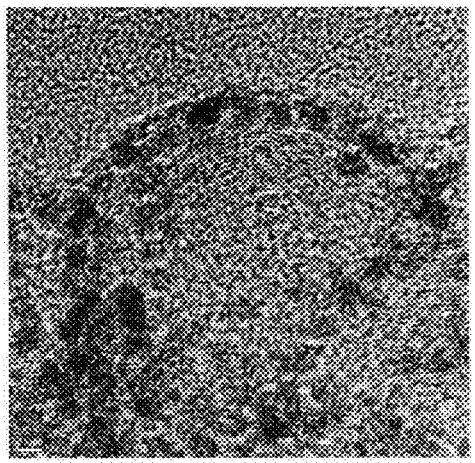
Figure 16G:
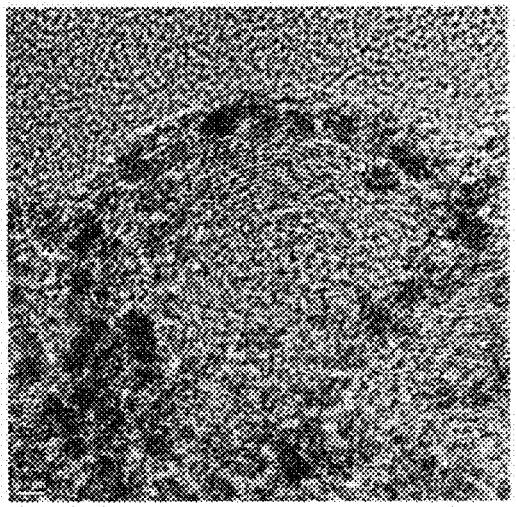
Figure 16H:
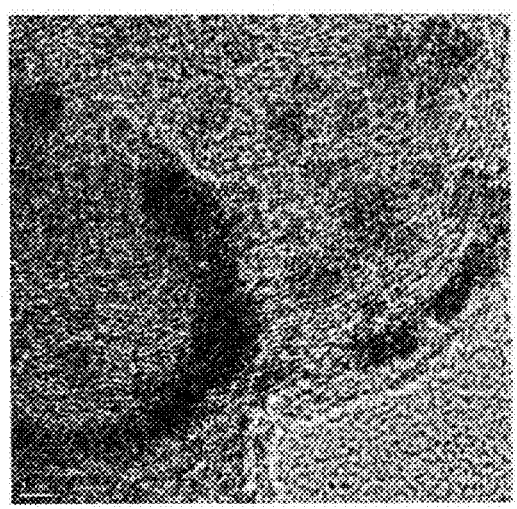
Figure 16I:
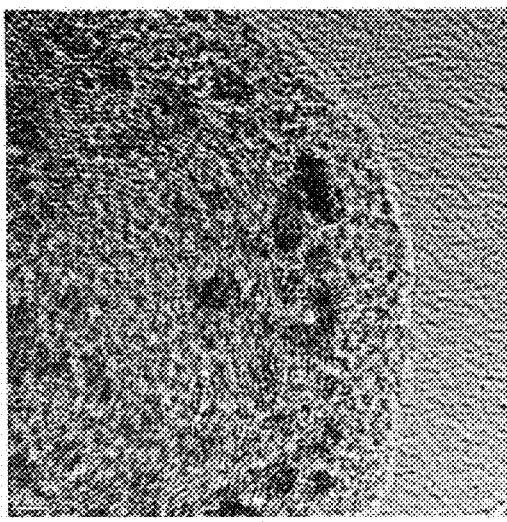
Figure 17A:
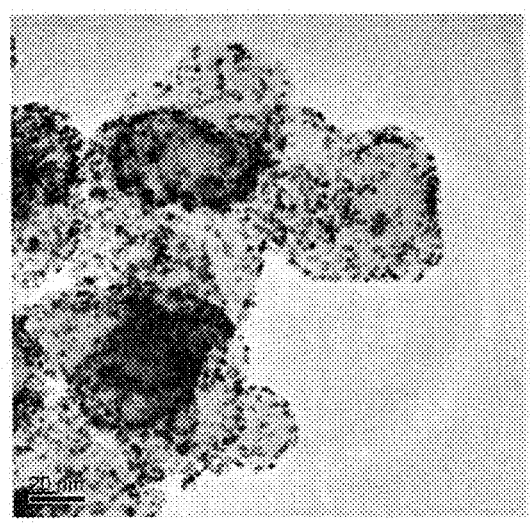
FIGS. 17a-17j are TEM images of a Pt/C-trien catalyst by using triethylenetetraamine as the chelating agent with 30% Pt loading in various areas in accordance with the eighth example of the present invention.
Figure 17B:
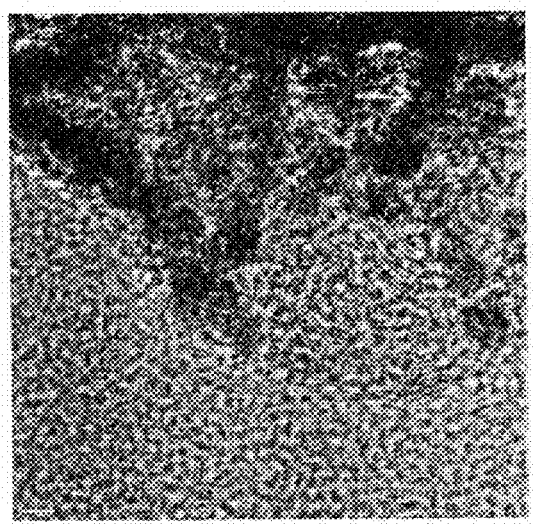
Figure 17C:
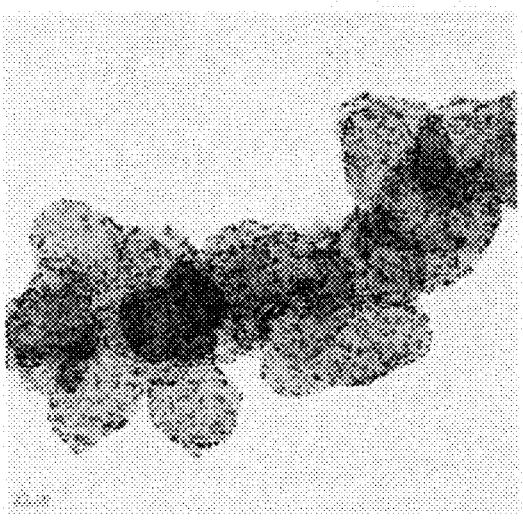
Figure 17D:
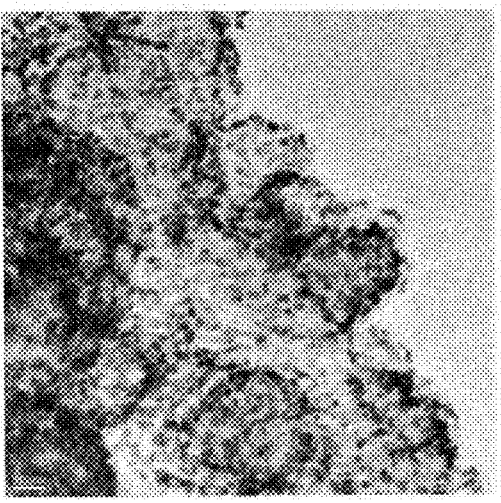
Figure 17E:
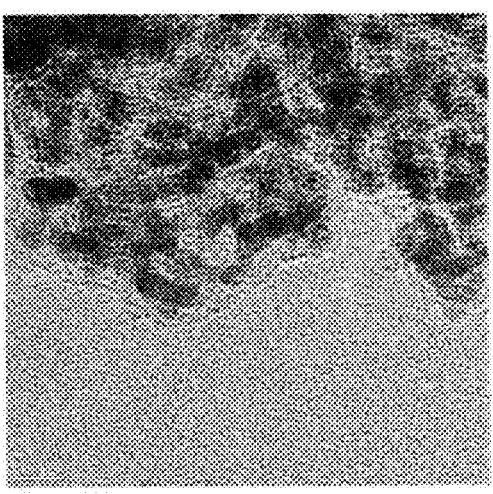
Figure 17F:
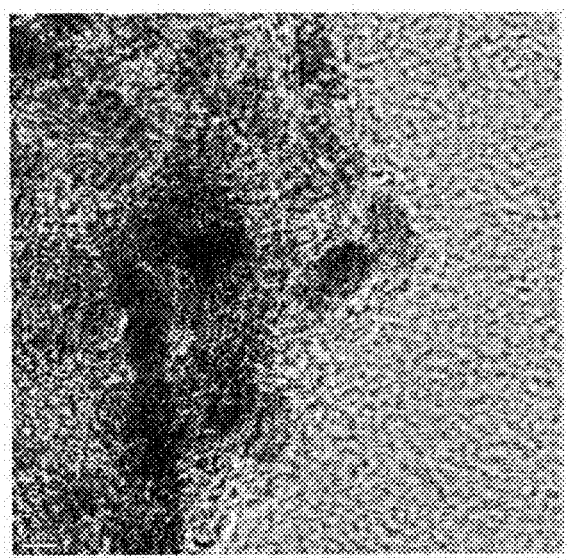
Figure 17G:
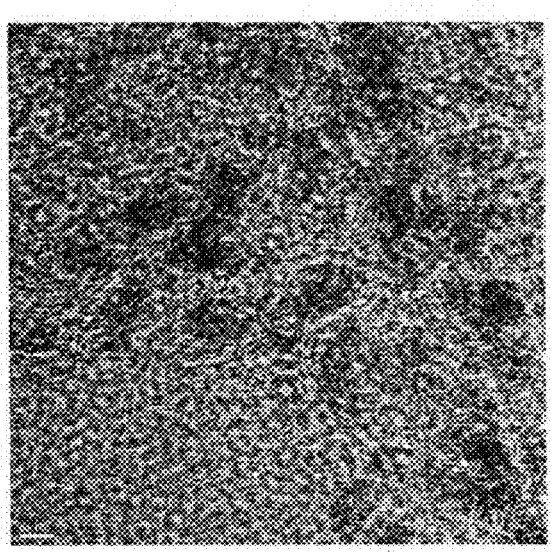
Figure 17H:
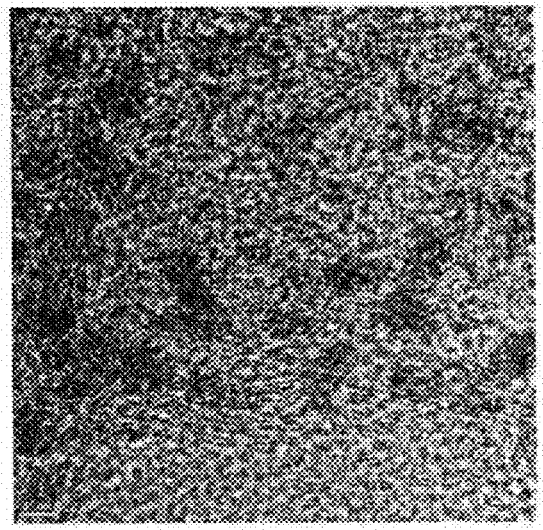
Figure 17I:
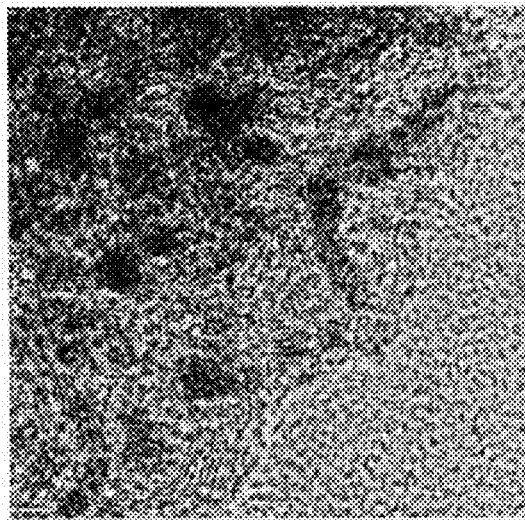
Figure 17J:
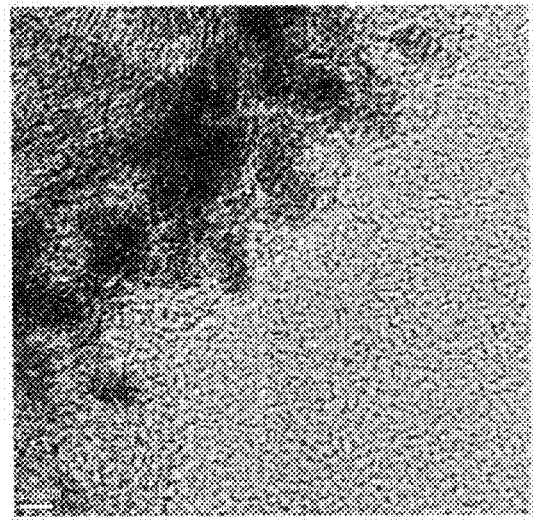
Figure 18A:
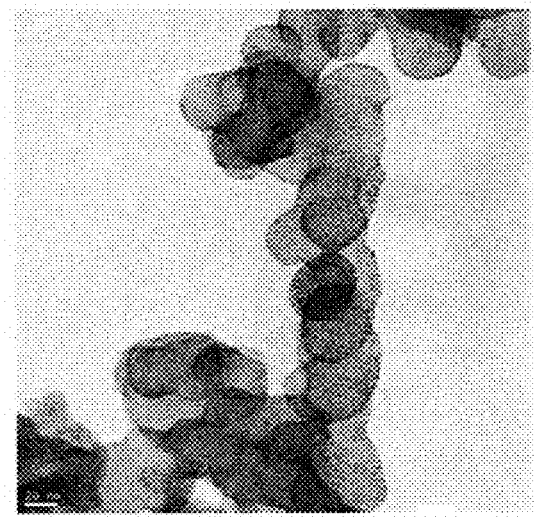
FIGS. 18a-18j are TEM images of a Pt/C-bpy catalyst by using 2,2'-bipyridine as the chelating agent with 18.7% Pt loading in various areas in accordance with a ninth example of the present invention.
Figure 18B:
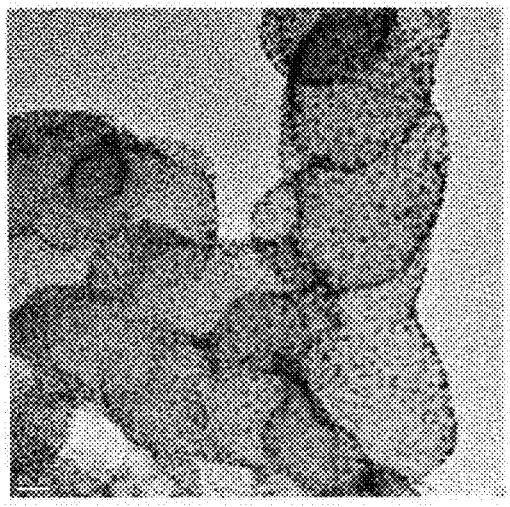
Figure 18C:
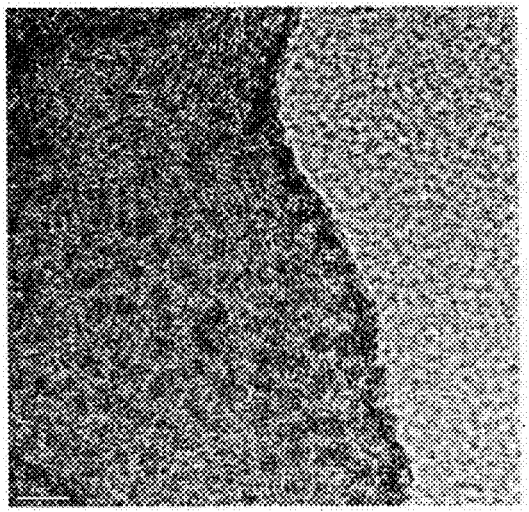
Figure 18D:
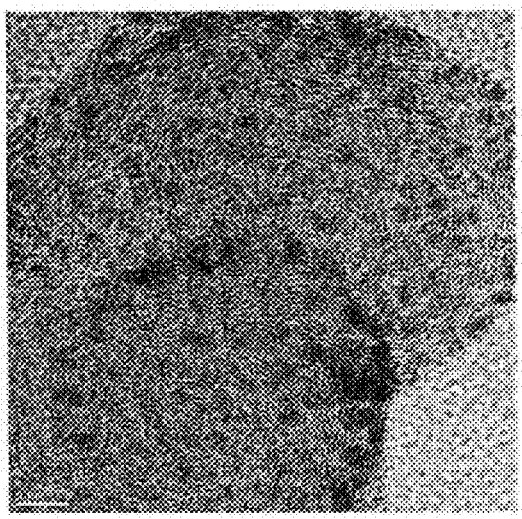
Figure 18E:
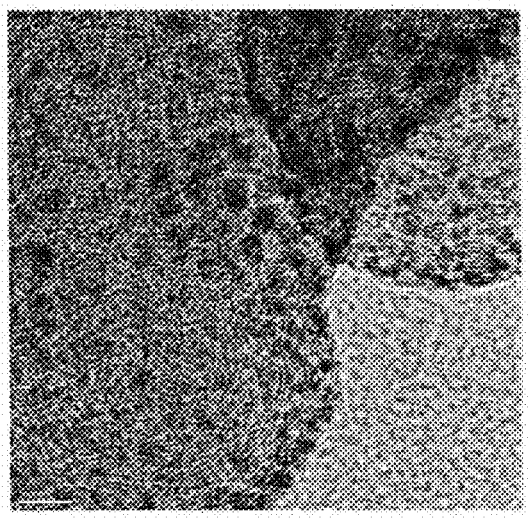
Figure 18F:
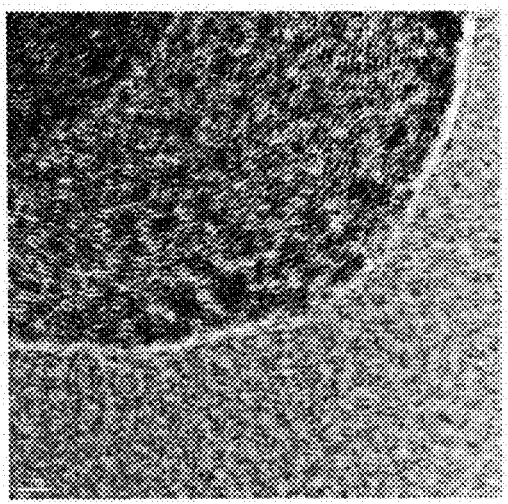
Figure 18G:
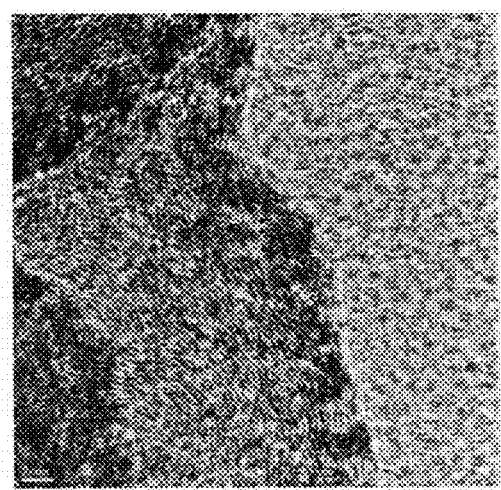
Figure 18H:
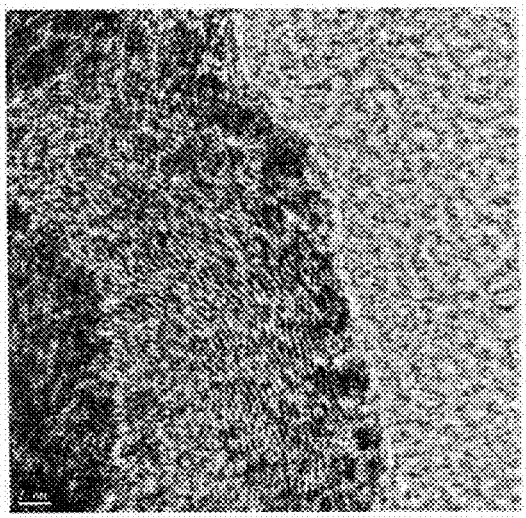
Figure 18I:
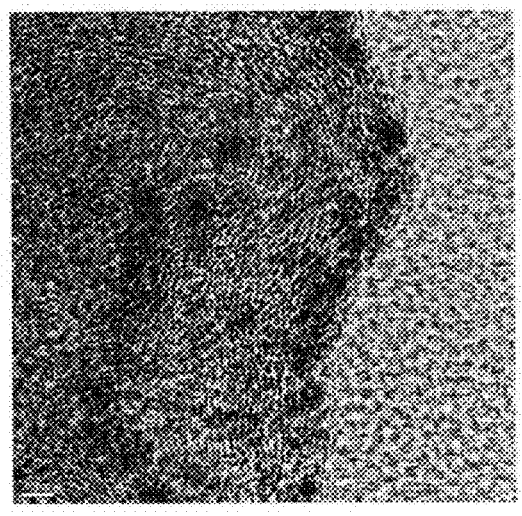
Figure 18J:
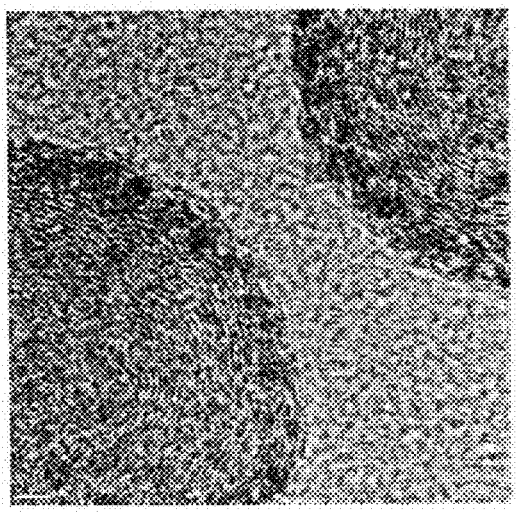
Figure 19A:
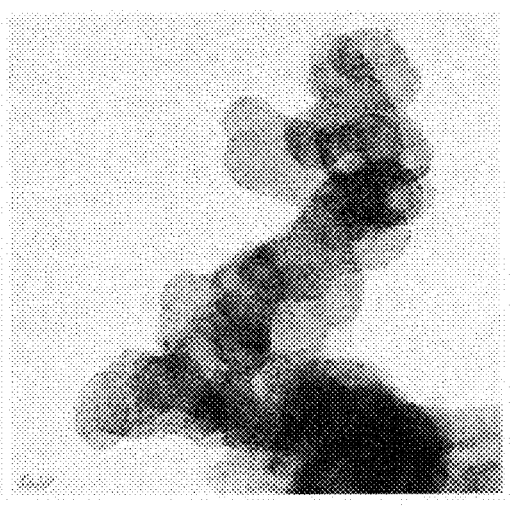
FIGS. 19a-19i are TEM images of a Pt/C-bpy catalyst by using 2,2'-bipyridine as the chelating agent with 30.2% Pt loading in various areas in accordance with the ninth example of the present invention.
Figure 19B:
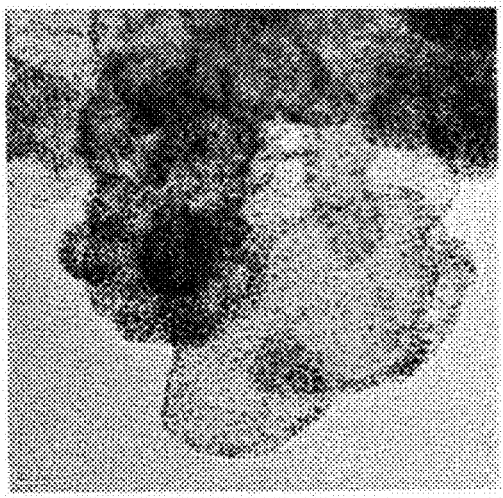
Figure 19C:
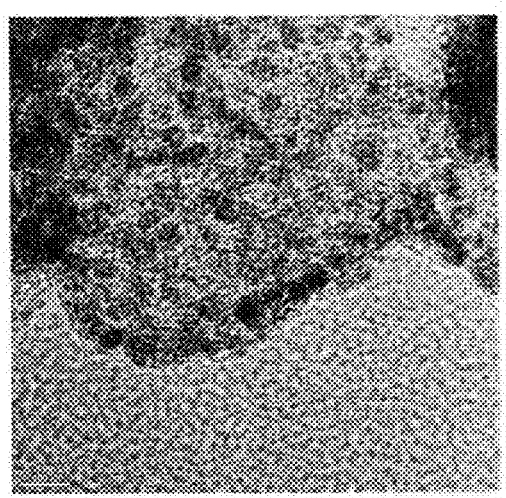
Figure 19D:
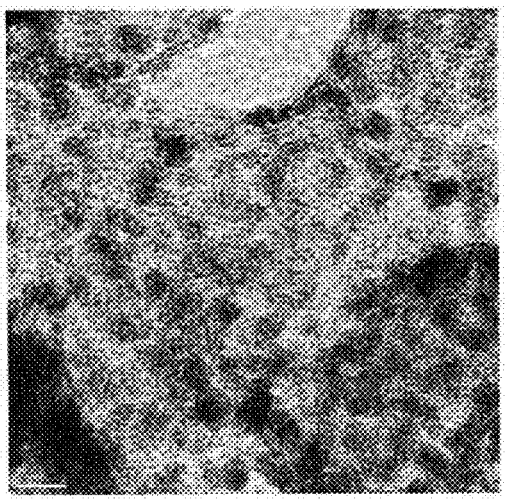
Figure 19E:
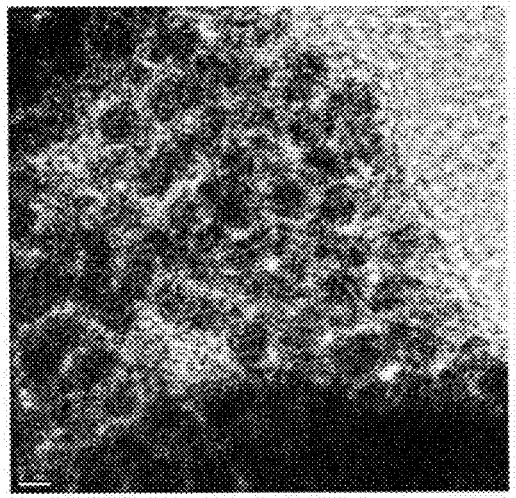
Figure 19F:
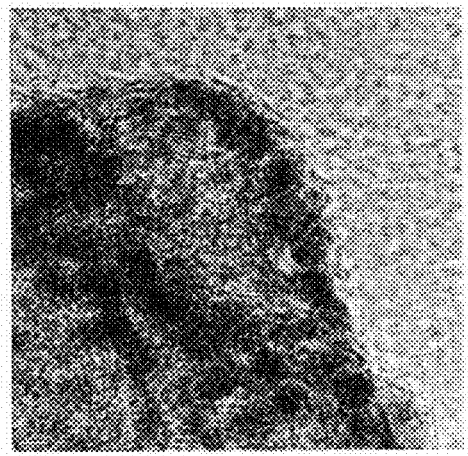
Figure 19G:
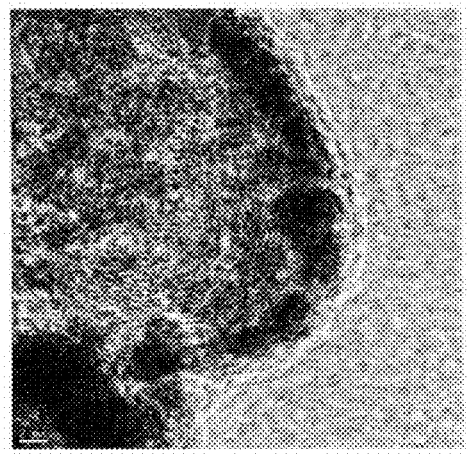
Figure 19H:
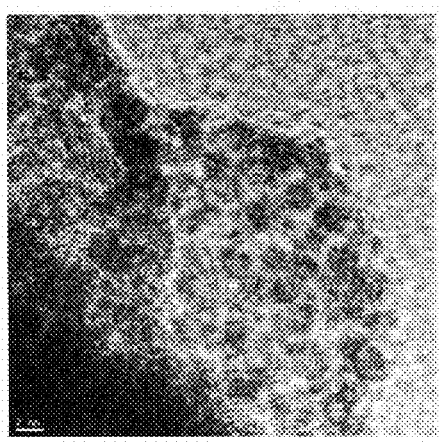
Figure 19I:
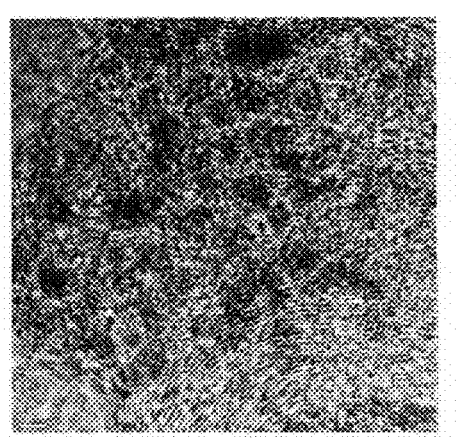

The manufacturing method of the platinum catalyst on the supports of a fifth example according to the preferred teachings of the present invention is the same as the first example as described above and therefore not described in detail to avoid redundancy. The only difference between the fifth and the first examples is that the chelating agent used in the fifth example is 2,2'-Bipyridine to form the platinum complex of $Pt[bpy]_2^{2+}$ wherein the chelating agent with 52 mg and chloroplatinic acid with 26.1 ml are used. Referring to FIG. 8, the mean particle size of Pt/C-bpy catalyst is 1.92 nm. Standard deviation is 0.4 nm. As a result, particle size distribution of the present invention is narrow. Besides, referring to FIGS. 13a to 13c, according to various magnifications of TEM, Pt nanoparticles are highly dispersed on the supports of carbon black.

The manufacturing method of the platinum catalyst on the supports of a sixth example according to the preferred teachings of the present invention is the same as the first example as described above and therefore not described in detail to avoid redundancy. The only difference between the sixth and the first examples is that the chelating agent used in the sixth example is 1,10-phenanthroline to form the platinum complex of $Pt[phen]_2^{2+}$ wherein the chelating agent with 60 mg and chloroplatinic acid with 26.1 ml are used. The mean particle size of Pt/C-phen catalyst is 1.6 nm. Standard deviation is 0.22 nm.

Figure 9A:
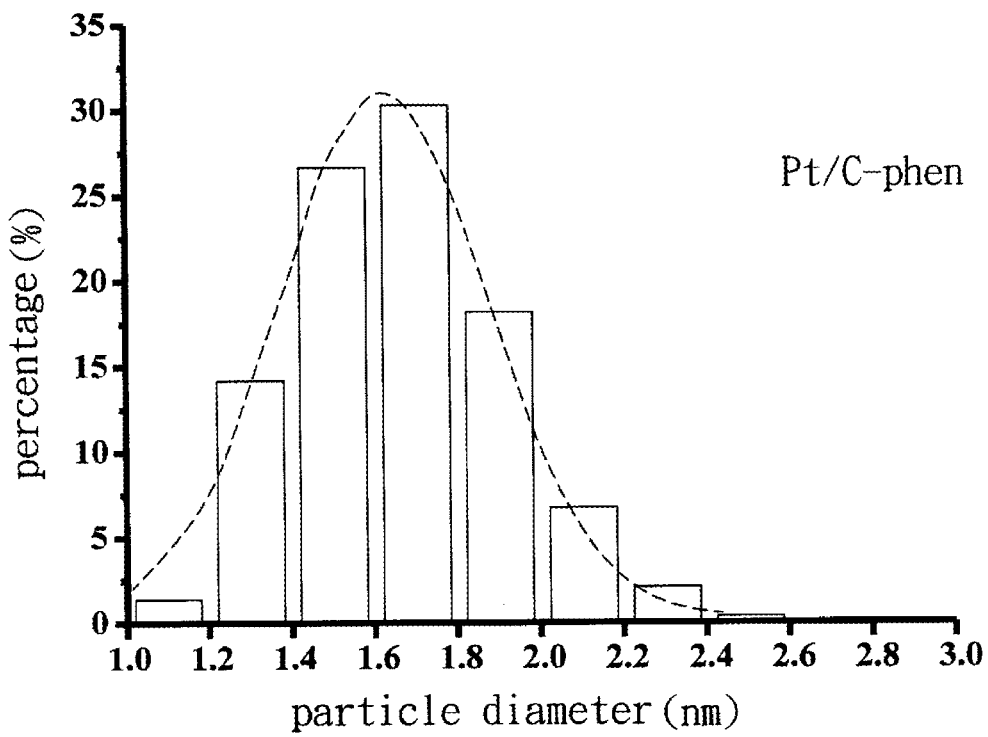
FIGS. 9a-b are histrograms of the particle size distribution for a Pt/C-phencatalyst in accordance with the preferred embodiment of the present invention.
Figure 9B:
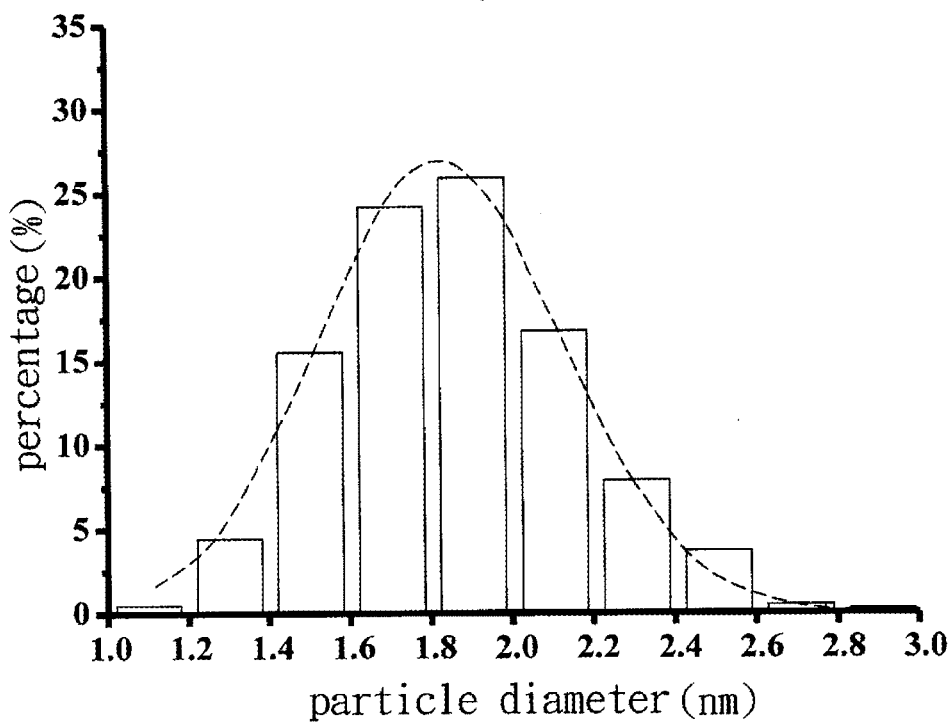

The manufacturing method of the platinum catalyst on the supports of a seventh example according to the preferred teachings of the present invention is the same as the first example as described above and therefore not described in detail to avoid redundancy. The only difference between the seventh and the first examples is that the chelating agent used in the seventh example is 1,10-phenanthroline to form the platinum complex of $Pt[phen]_2^{2+}$ wherein the loading of Pt with respect to carbon black is 0.33, 0.67, 1 mmol for Pt/C-phen-1, Pt/C-phen-2, and Pt/C-phen-3 catalysts, respectively. Regarding to the table 3 and FIGS. 9a to 9b, for the platinum catalyst, even in high Pt loading such as 21.4% or 30%, the platinum catalyst with narrow particle size distribution and with highly dispersion still can be obtained. By transmission electron microscope (TEM), the morphology of Pt distribution can be observed and the Pt particle size can be measured. Besides, regarding to FIGS. 14a to 14k, the morphology of Pt distribution with 21.4% Pt loading in various areas is observed. Regarding to FIGS. 15a to 15k, the morphology of Pt distribution with 30% Pt loading in various areas is observed. As a result, even increasing Pt loading of the platinum catalyst, well-distributed platinum catalyst on the supports without agglomeration still can be obtained.

TABLE 3 nanoparticle size, particle size distribution, and yield according to various Pt loading by the chelating agent of 1,10-phenanthroline.

| Precursor | Pt/C-x | Particle size (nm) | Standard deviation (nm) | Particle size distribution (nm) | Pt loading (wt. %) |
| --- | --- | --- | --- | --- | --- |
| $Pt[phen]_2^{2+}$ | Pt/C-phen | 1.6 | 0.2 | 1.1~2.5 | 7.5 |
| | | 1.63 | 0.2 | 1~2.6 | 21.4 |
| | | 1.82 | 0.3 | 1~2.8 | 30.0 |

The manufacturing method of the platinum catalyst on the supports of a eighth example according to the preferred teachings of the present invention is the same as the first example as described above and therefore not described in detail to avoid redundancy. The only difference between the eighth and the first examples is that the chelating agent used in the eighth example is triethylenetetraamine to form the platinum complex of $Pt[trien]^{2+}$ wherein the loading of Pt with respect to carbon black is 0.33, 0.67, 1 mmol respectively. Regarding to FIGS. 16a to 16i, the morphology of Pt distribution with 15.5% Pt loading in various areas is observed. Regarding to FIGS. 17a to 17j, the morphology of Pt distribution with 30% Pt loading in various areas is observed. As a result, even if the loading of Pt is around 15.5% or 30%, the platinum catalyst with narrow particle size distribution and with highly dispersion still can be obtained. Therefore, even increasing Pt loading of the platinum catalyst, well-distributed platinum catalyst on the supports without agglomeration still can be obtained. Besides, referring to table 4, particle size distribution of the platinum catalyst is narrow and the dispersion thereof is uniform with various Pt loading.

TABLE 4 nanoparticle size, particle size distribution, and Pt loading according to various Pt loading.

| Precursor | Pt/C-x | Particle size (nm) | Standard deviation (nm) | Particle size distribution (nm) | Pt loading (wt. %) |
| --- | --- | --- | --- | --- | --- |
| $Pt[trien]^{2+}$ | Pt/C-trien | 1.7 | 0.3 | 1.1~2.5 | 9.80 |
| | | 2.08 | 0.3 | 1.2~3.0 | 15.5 |
| | | 2.48 | 0.3 | 1.6~3.2 | 30.0 |

The manufacturing method of the platinum catalyst on the supports of a ninth example according to the preferred teachings of the present invention is the same as the first example as described above and therefore not described in detail to avoid redundancy. The difference between the ninth and the first examples is that the chelating agent used in the ninth example is 2,2'-bipyridine to form the platinum complex of [Pt(bpy)$_2$]$^{2+}$ wherein the loading of Pt with respect to carbon black is 0.33, 0.67, 1 mmol for Pt/C-bpy-1, Pt/C-bpy-2, and Pt/C-bpy-3 catalysts, respectively. Moreover, the mole ratio of the chelating agent to Pt is 2:1. Besides, the solvent of the ninth example is the ethanol-water solution which the ratio of ethanol to water is 1:4. Regarding to table 5, even increasing Pt loading of the platinum catalyst, well-distributed platinum catalyst on the supports without agglomeration still can be obtained. Regarding to FIGS. 18a to 18j, the morphology of Pt distribution with 18.7% Pt loading in various areas is observed. Besides, regarding to FIGS. 19a to 19i, the morphology of Pt distribution with 30.2% Pt loading in various areas is observed. As a result, even if the loading of Pt is around 18.7% or 30.2%, the platinum catalyst with narrow particle size distribution and with highly dispersion still can be obtained.

TABLE 5 nanoparticle size, particle size distribution, and yield according to various Pt loading by the chelating agent of 2,2'-bipyridine.

| Pt/C-x | Particle size (nm) | Particle size distribution (nm) | Pt loading (wt. %) | Yield (%) |
|---|---|---|---|---|
| Pt/C-bpy-1 | 1.7 | 1.1~2.9 | 8.4 | 84 |
| Pt/C-bpy-2 | 1.9 | 1.0~3.0 | 18.7 | 96 |
| Pt/C-bpy-3 | 2.0 | 1.3~2.9 | 30.2 | 99 |
| Pt/C-ETEK | 2.6 | 1.2~4.3 | 20 | — |

Moreover, the platinum catalyst on the supports of the present invention can be used in proton exchange membrane fuel cell (PEMFC). The platinum catalyst on the supports is applied on Nafion® 212 membrane to make membrane electrode assembly (MEA). In detail, the Pt/C catalyst is added into a mixed solution with a solvent such as ethanol or isopropyl alcohol and 5 wt. % of Nafion® solution. Following, the mixed solution with Pt/C catalyst is sprayed on one or two substrates such as carbon clothes and then membrane electrode assembly (MEA) is integrated between two carbon clothes by conventional hot press for 90 seconds. The temperature of hot press is around 135° C. The pressure of hot press is around 50 kg/cm$^2$. In addition, the Pt/C catalyst of the present invention is better to be used on anode and cathode at the same time.

F. Selected Area Electron Diffraction Patterns (SADP)

Referring to FIGS. 10d, 11d, 12d, and 13d, various Pt/C catalysts of Pt/C-dien, Pt/C-trien, Pt/C-en, and Pt/C-bpy are analyzed under respective selected area electron diffraction patterns (SADP). The SADP of particles in FIGS. 10d, 11d, 12d, and 13d indicate that the particles possess a face-centered cubic (fcc) Pt phase and have high crystalline.

G. X-Ray Diffractometer (XRD)

Figure 20:
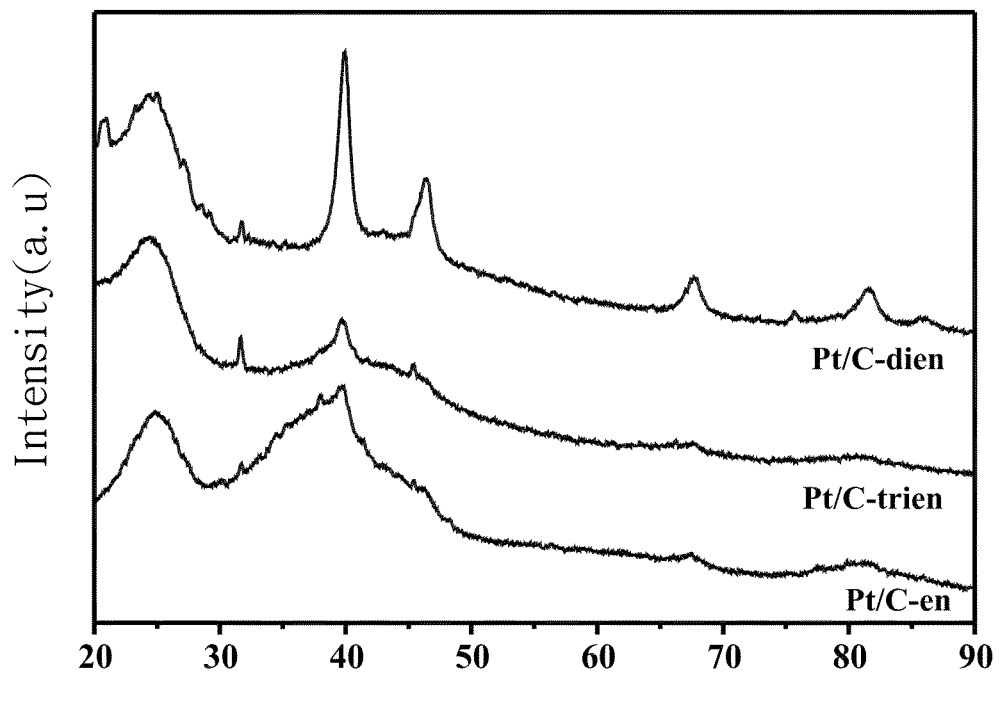
FIG. 20 is a XRD graph of platinum catalysts of Pt/C-en, Pt/C-dien, and Pt/C-trien in accordance with the preferred embodiment of the present invention.
Figure 21:
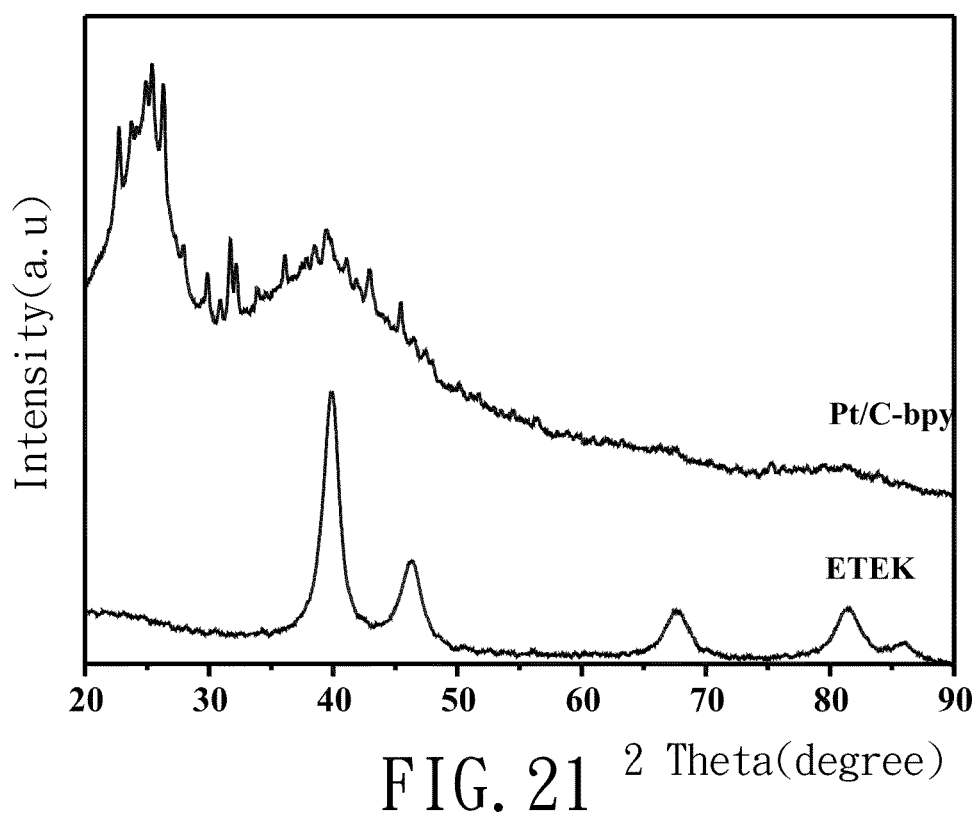
FIG. 21 is a XRD graph of the Pt/C-bpy catalyst in accordance with the preferred embodiment of the present invention.
Figure 22:
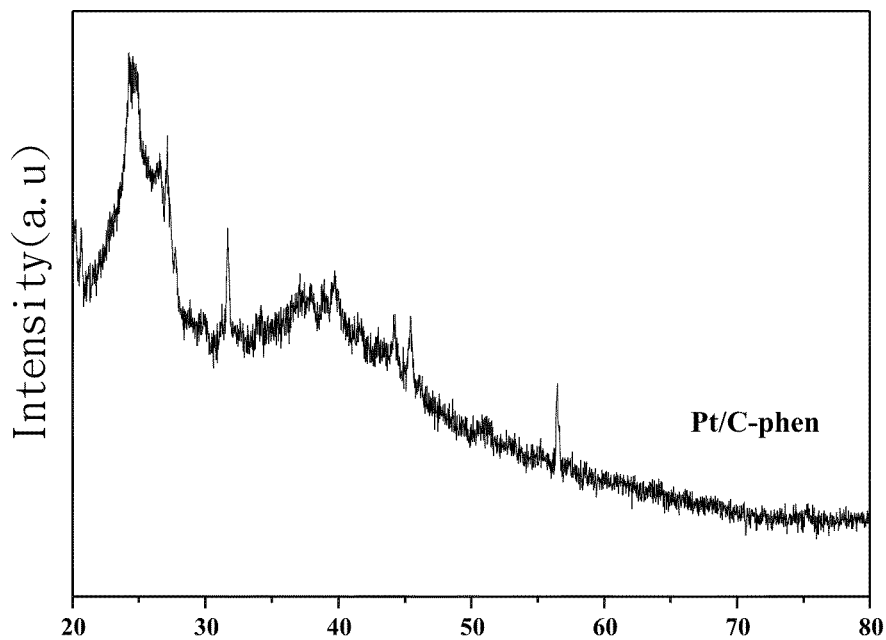
FIG. 22 is a XRD graph of the Pt/C-phencatalyst in accordance with the preferred embodiment of the present invention.

Referring to FIGS. 20 to 22, the X-ray diffractometer (XRD) patterns of the platinum catalyst on the supports are shown. The broad diffraction peak at around 25° belongs mostly to the (0 0 2) plane of the hexagonal structure of Vulcan XC-72 carbon. The characteristic diffraction peaks of Pt are recognized at about 39°, 46°, 66° and 81° can be indexed as (1 1 1), (2 0 0), (2 2 0) and (3 1 1) reflections of the fcc phase of bulk Pt. Estimations of the mean Pt nanoparticle size using the Scherrer equation show similar relative size differences between the Pt/C-x catalysts as obtained in the TEM investigation.

H. Cyclic Voltammograms (CV)

Figure 23:
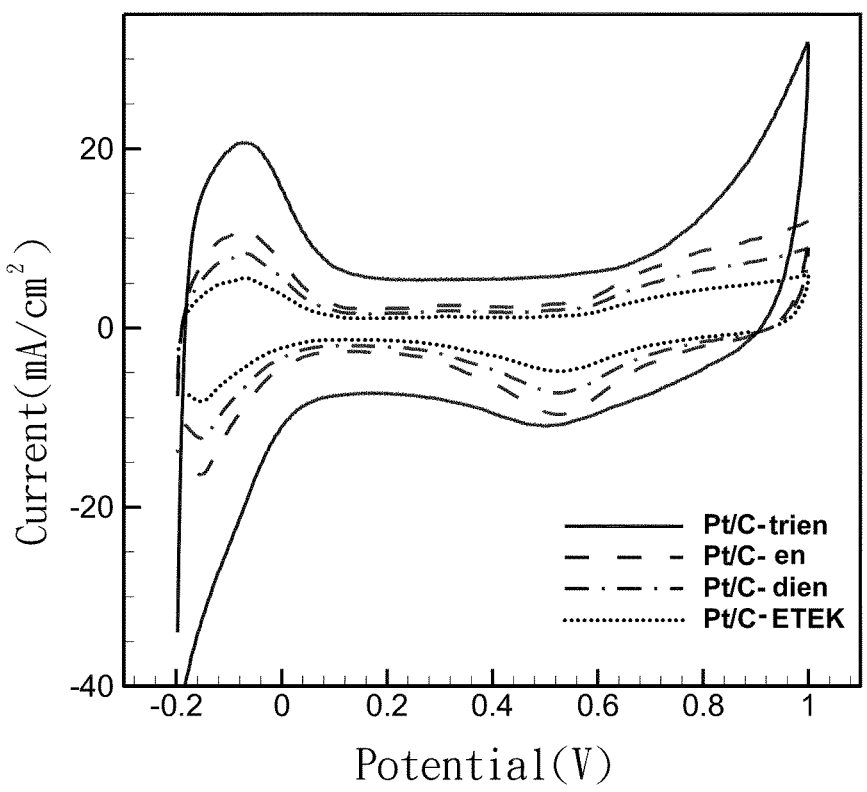
FIG. 23 is sets of cyclic voltammographs (CV) of the platinum catalysts of Pt/C-en, Pt/C-dien, and Pt/C-trien in accordance with the first to third examples of the present invention.
Figure 24:
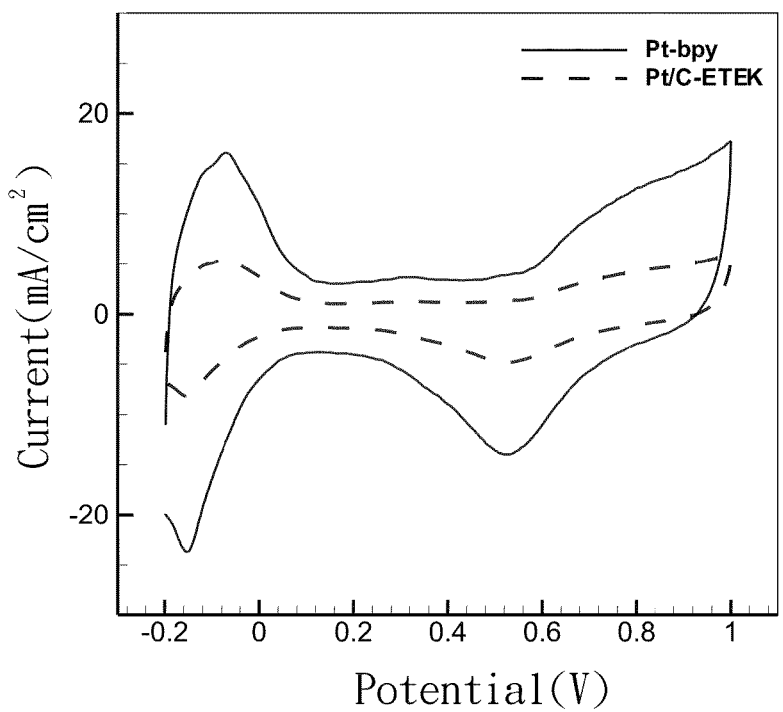
FIG. 24 is sets of cyclic voltammographs (CV) of the Pt/C-bpy catalyst in accordance with the fifth example of the present invention.
Figure 25:
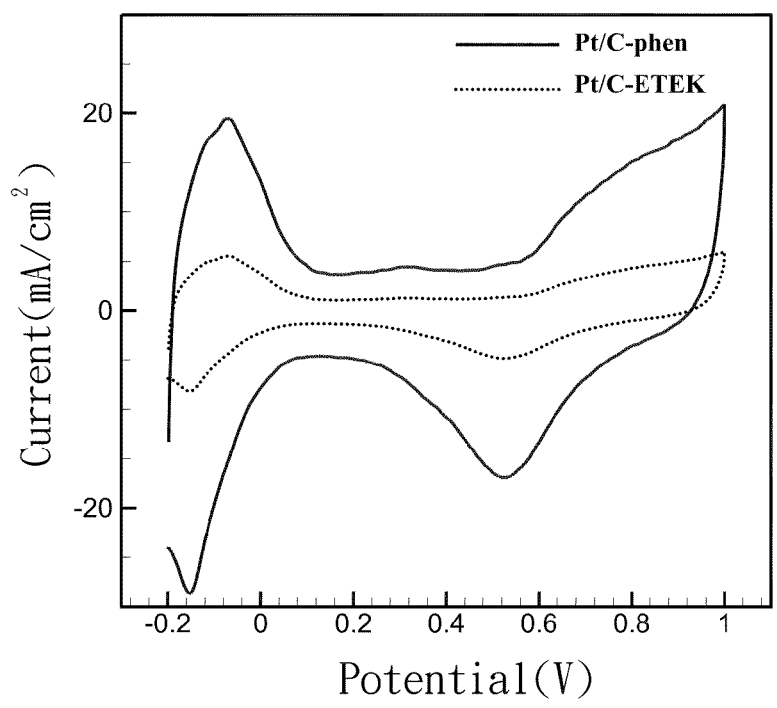
FIG. 25 is sets of cyclic voltammographs (CV) of the Pt/C-phen catalyst in accordance with the sixth example of the present invention.

Cyclic voltammetry (CV) curves between 0 and 1.2 V vs Ag/AgCl electrode are recorded for the platinum catalyst on the supports (a Pt/C catalyst) prepared in the present invention. Testing sample is prepared by mixing 20 mg of the platinum catalyst on the supports, 120 μl ethanol, 20 μl and a commercial 5 wt. % of Nafion® solution together and sonicated for 30 mins to get a paste solution. Following, around 25 μl of the paste solution is applied onto a glassy carbon disk with a sectional area of 0.066 cm$^2$ and then dried in room temperature to form a thin film on surface of the carbon disk. The electrochemical measurements are performed in 80 ml of 0.5 M sulfuric acid (H$_2$SO$_4$) at 25□. Prior to the electrochemical measurements, the paste solution is purged with nitrogen for working electrode activation. The chelating agent is selected from diethylenetriamine, triethylenetetraamine, ethylenediamine, 1,10-phenanthroline, and 2,2'-Bipyridine to form the platinum complexes in the forms of Pt[dien)]$^{2+}$, Pt[trien]$^{2+}$, Pt[en]$_2$$^{2+}$, [Pt(phen)$_2$]$^{2+}$, and [Pt(bpy)$_2$]$^{2+}$, respectively. Therefore, the platinum catalysts with carbon black as the supports can be obtained and are abbreviated as Pt/C-dien, Pt/C-trien, Pt/C-en, Pt/C-phen, and Pt/C-bpy, respectively. Referring to FIG. 23, the electrochemical activity of the platinum catalysts of Pt/C-dien, Pt/C-trien, or Pt/C-en is better than the commercial Pt-based catalyst (Pt/C-ETEK). The order of active surface area is Pt/C-trien>Pt/C-en>Pt/C-dien. In addition, referring to FIGS. 24 and 25, the electrochemical activity of the platinum catalysts (Pt/C-x), which 2,2'-Bipyridine and 1,10-phenanthroline are used as the chelating agents respectively is also better than the commercial Pt-based catalyst (Pt/C-ETEK) and the active surface area thereof is larger than Pt/C-ETEK catalyst. As a result, catalytic activity of the present invention is better than Pt/C-ETEK catalyst.

Figure 26:
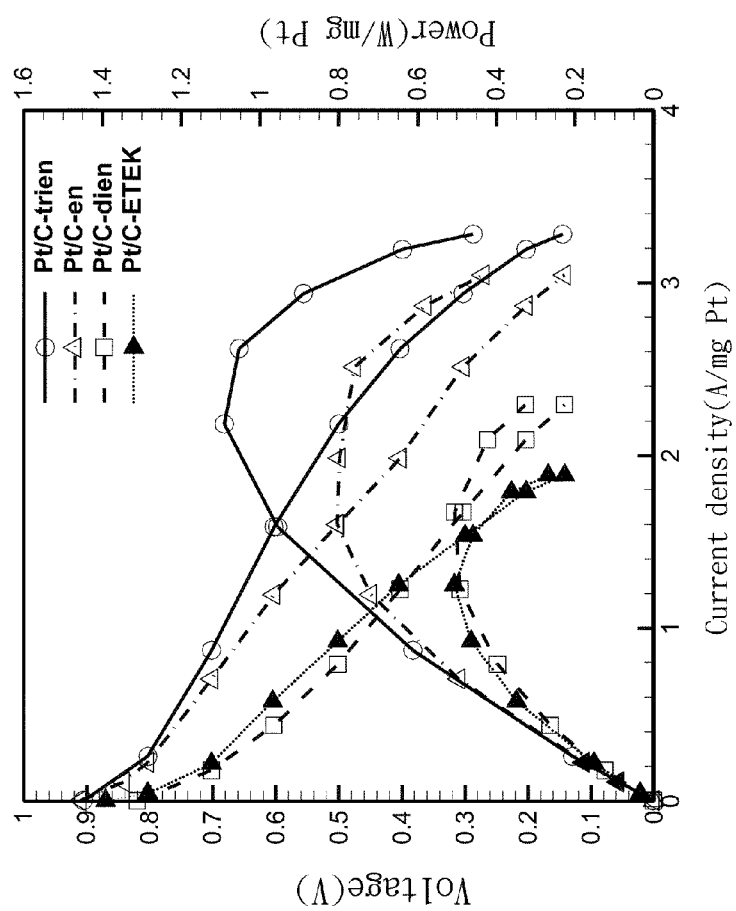
FIG. 26 is curves of voltage and power vs. current density of the FIG. 23.
Figure 27:
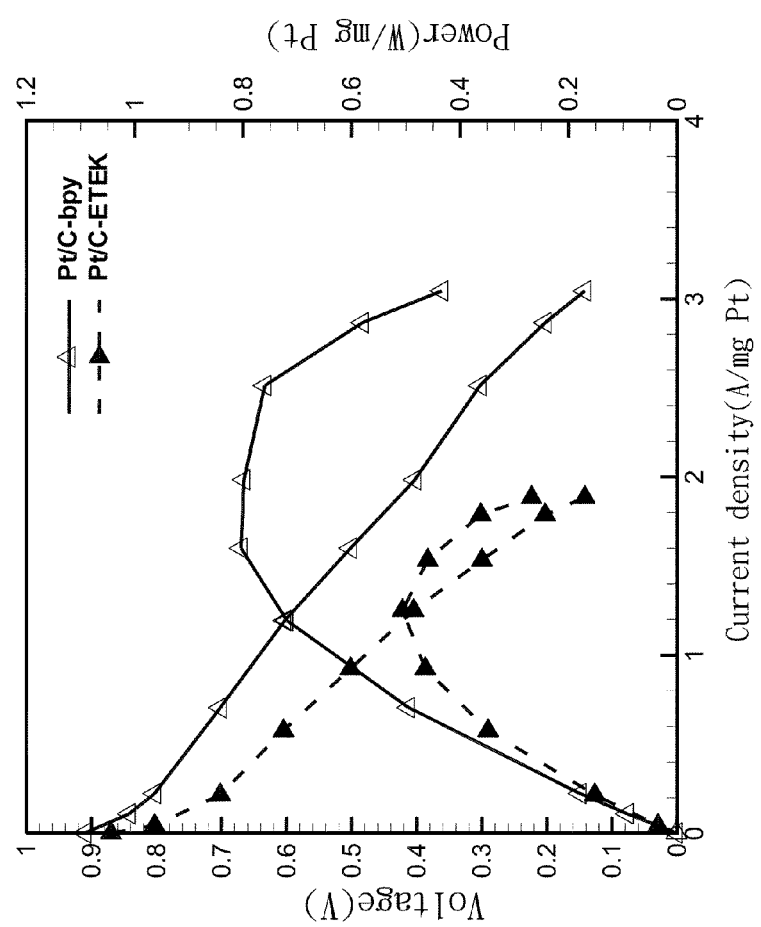
FIG. 27 is curves of voltage and power vs. current density of the FIG. 24.
Figure 28:
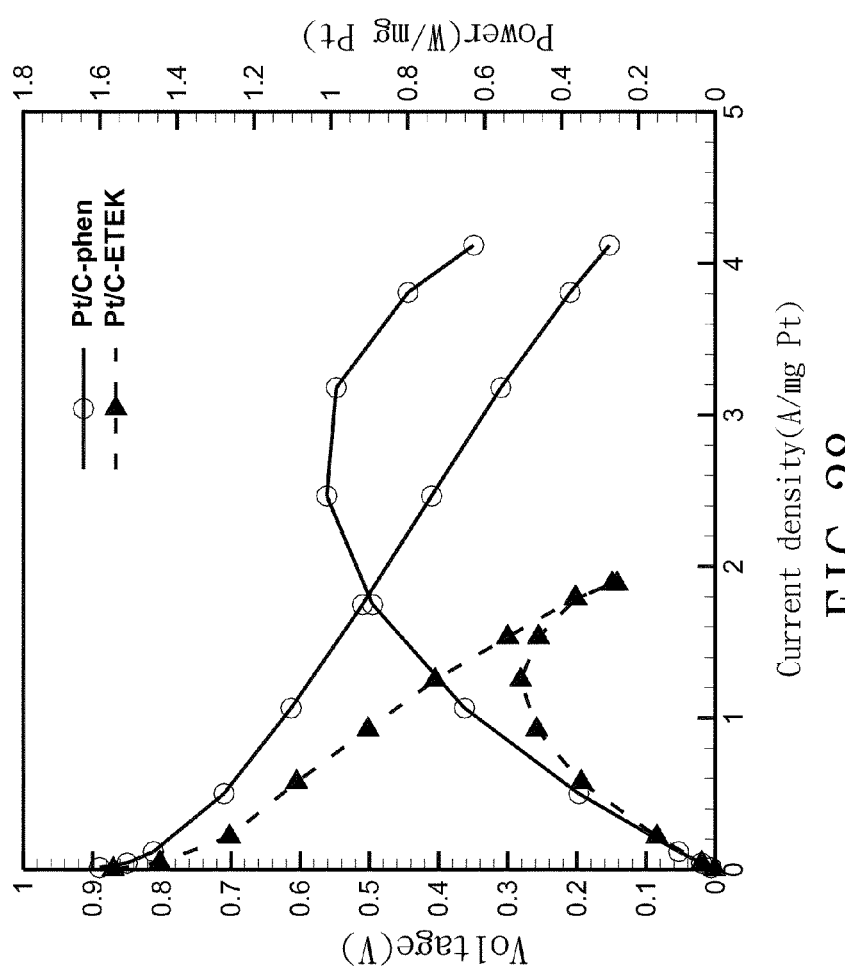
FIG. 28 is curves of voltage and power vs. current density of the FIG. 25.

I. Testing for a Single Cell:

For measuring performance of MEA, single cell operates MEA in 0.5V. Under 24 hours of operation in the fuel cell, a stable current density and polarization curves can be obtained. Regarding to FIGS. 26 to 28, the current density of the platinum catalyst containing 12 wt. % Pt loading according to the preferred teachings of the present invention is already about ¼ that of the commercial Pt-based catalyst containing 40 wt % Pt loading.

Figure 29:
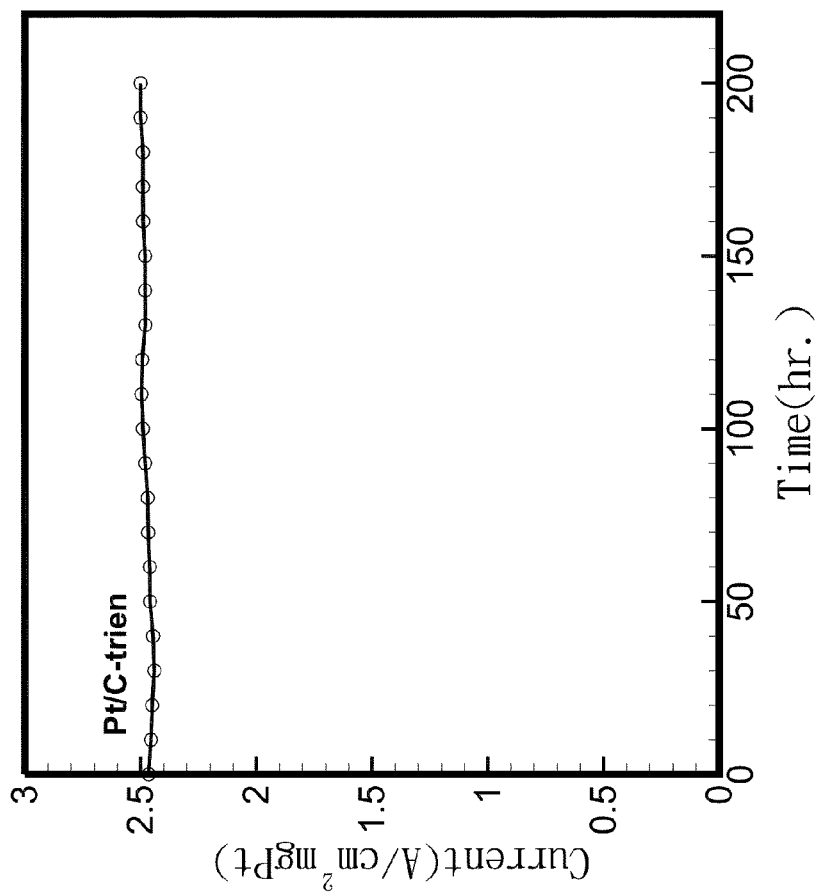
FIG. 29 is a diagram for stability test in accordance with the second example of the present invention.
Figure 30:
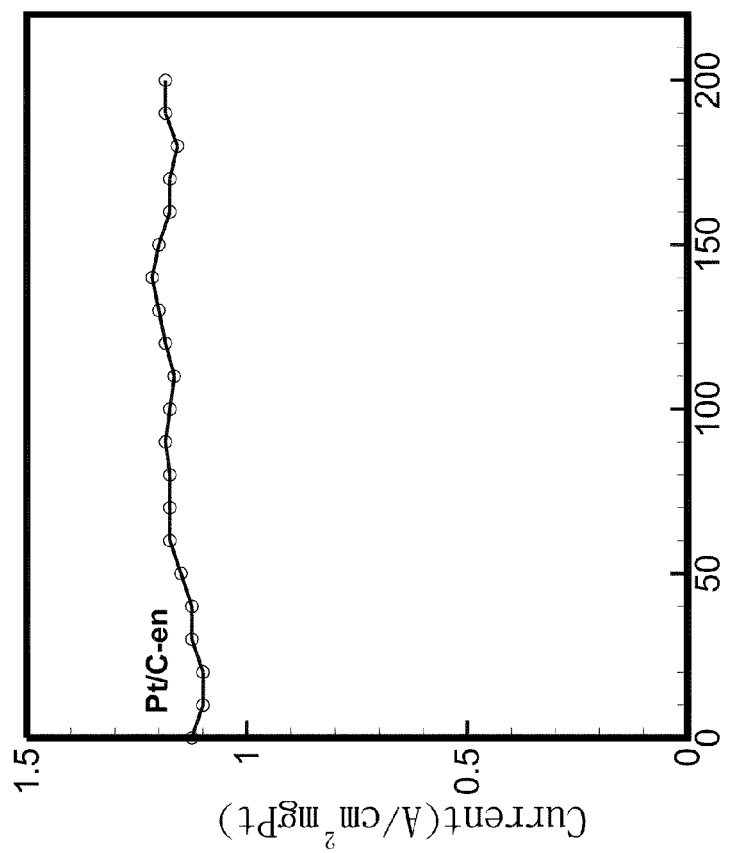
FIG. 30 is a diagram for stability test in accordance with the third example of the present invention.
Figure 31:
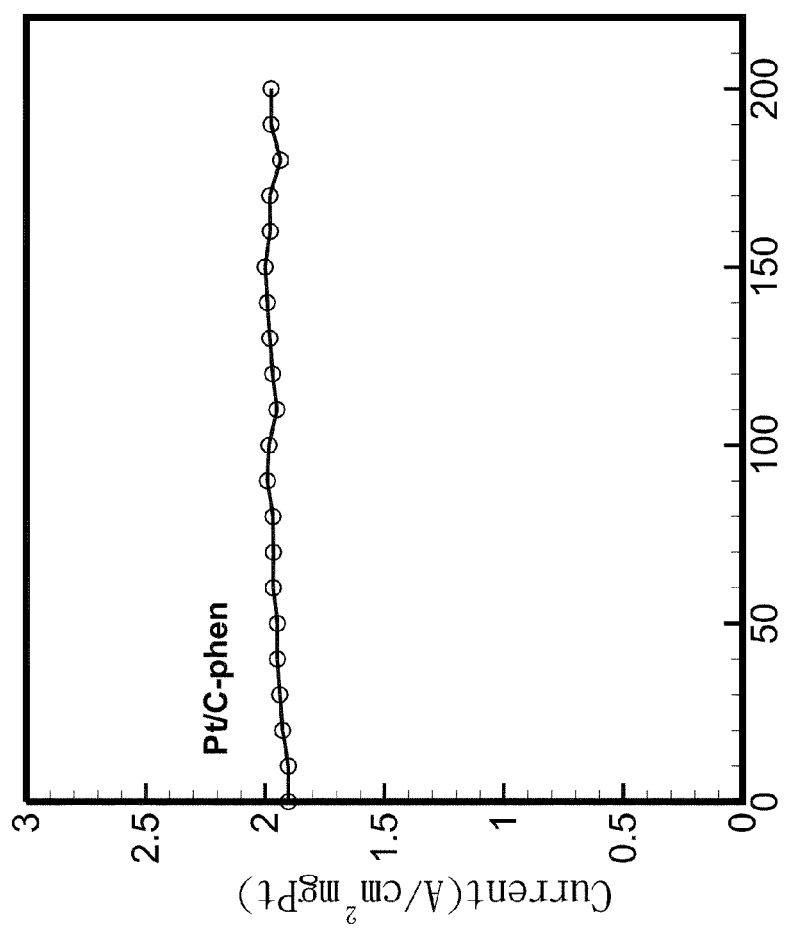
FIG. 31 is a diagram for stability test in accordance with the sixth example of the present invention.

In addition, referring to FIGS. 29 to 31, the stability of the platinum catalyst on the supports of the present invention is quite stable. Please referring to reference of S.-J. Liu, C.-H. Huang, C.-K. Huang, W.-S. Hwang, Chem. Comm. (2009) for more related testing results.

Thus since the invention disclosed herein may be embodied in other specific forms without departing from the spirit or general characteristics thereof, some of which forms have been indicated, the examples described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A process for producing a platinum complex comprising: mixing chloroplatinic acid and a chelating agent with a solvent, wherein the solvent is sonicated after the chloroplatinic acid and the chelating agent are added into the solvent, wherein [PtCl$_6$]$^{2-}$ ions of the chloroplatinic acid is reacted with the chelating agent to form a platinum complex, wherein the mole ratio of the chelating agent to Pt is 2:1, with the chelating agent being ethylenediamine or 1,10-phenanthroline, wherein the solvent is sonicated for 4 to 6 hours.

* * * * *